(12) United States Patent
Annaert et al.

(10) Patent No.: US 8,790,887 B2
(45) Date of Patent: Jul. 29, 2014

(54) SCREENING METHODS FOR COMPOUNDS THAT MODULATE ARF-6 MEDIATED ENDOSOMAL REDISTRIBUTION

(75) Inventors: Wim Annaert, Kontich (BE); Ragna Sannerud, Leuven (BE); Katrijn Coen, Westerlo (BE); Bart De Strooper, Leuven (BE)

(73) Assignees: VIB VZW, Ghent (BE); Katholieke Universiteit Leuven, K.U. Leuven R&D, Leuven (BE)

( * ) Notice: Subject to any disclaimer, the term of this patent is extended or adjusted under 35 U.S.C. 154(b) by 0 days.

(21) Appl. No.: 13/512,851

(22) PCT Filed: Dec. 6, 2010

(86) PCT No.: PCT/EP2010/069000
§ 371 (c)(1),
(2), (4) Date: Jul. 5, 2012

(87) PCT Pub. No.: WO2011/067420
PCT Pub. Date: Jun. 9, 2011

(65) Prior Publication Data
US 2012/0276076 A1 Nov. 1, 2012

Related U.S. Application Data

(60) Provisional application No. 61/283,476, filed on Dec. 4, 2009.

(51) Int. Cl.
C12Q 1/37 (2006.01)

(52) U.S. Cl.
USPC ............................................................. 435/23

(58) Field of Classification Search
USPC ............................................................. 435/23
See application file for complete search history.

(56) References Cited

U.S. PATENT DOCUMENTS

| | | | |
|---|---|---|---|
| 5,693,761 | A | 12/1997 | Queen et al. |
| 5,766,886 | A | 6/1998 | Studnicka et al. |
| 5,821,123 | A | 10/1998 | Studnicka et al. |
| 5,859,205 | A | 1/1999 | Adair et al. |
| 5,869,619 | A | 2/1999 | Studnicka et al. |
| 6,054,297 | A | 4/2000 | Carter |
| 6,180,370 | B1 | 1/2001 | Queen et al. |
| 2003/0143732 | A1 | 7/2003 | Fosnaugh et al. |
| 2004/0005590 | A1* | 1/2004 | Yan et al. ............... 435/6 |
| 2004/0208862 | A1* | 10/2004 | Brady-Kalnay et al. ..... 424/94.6 |
| 2012/0276076 | A1* | 11/2012 | Annaert et al. ............ 424/94.6 |

FOREIGN PATENT DOCUMENTS

| | | |
|---|---|---|
| EP | 626390 B1 | 11/2001 |
| WO | 2011/067420 A1 | 6/2011 |

OTHER PUBLICATIONS

Sakurai T. et al. Membrane Microdomain Switching. J Cell Biology 183(2)339-352, Oct. 20, 2008.*
Hill K. et al. Munc18 Interacting Proteins. J of Biological Chemistry 278(38)36032-40, Sep. 19, 2003.*
D'Souza-Schorey C. et al. ARF Proteins: Roles in Membrane Traffic and Beyond. Nature Reviews 7:347-358, May 2006.*
Annaert W. Sorting Out the Cell Biology of AD. Molecular Degeneration 7(Suppl 1)L6 Abstract, 2012.*
Sannerud R. et al. ADP Ribosylation Factor 6 (ARF6) Controls Amyloid Precursor Protein . . . PNAS 108(34)E559-568, Aug. 23, 2011.*
Schwarzman A. et al. Endogenous Presenilin 1 Redistributes to the Surface of Lamellipodia . . . Proc Natl Acad Sci 96:7932-7937, Jul. 1999.*
Steiner H. et al. A Loss of Function Mutation of Presenilin-2 Interferes with Amyloid Beta Peptide Production and Notch Signaling. J of Biological Chemistry 274(40)28669-73, Oct. 1999.*
Jaworski et al., ARF6 in the Nervous System, European Journal of Cell Biology, 2007, pp. 513-524, vol. 86, No. 9.
Database WPI, Week 200519, Thomson Scientific, London, GB, 2005, ZH Osaka, Bioscience Kenkyusho.
Schweitzer et al., A Requirement for ARF6 During the Completion of Cytokinesis, Experimental Cell Research, 2005, pp. 74-83, vol. 311, No. 1.
Rechards Marloes et al., Presenilin-1-Mediated Retention of APP Derivatives in Early Biosynthetic Compartments, Traffic, 2006, pp. 354-364, vol. 7 No. 3, Copenhagen, Denmark.
Hernandez-Deviez Delia et al., A Role for ARF6 and ARNO in the Regulation of Endosomal Dynamics in Neurons, Traffic, 2007, pp. 1750-1764, vol. 8, No. 12., Copenhagen, Denmark.
Beglopoulos et al., Regulation of CRE-Dependent Transcription by Presenilins: Prospects for Threapy of Alzheimer's Disease, Trends in Pharmacological Sciences, 2006, pp. 33-40, vol. 27, No. 1.
Nixon, Endosome Function and Dysfunction in Alzheimer's Disease and Other Neurodegenerative Diseases, Neurobiology of Aging, 2005, pp. 373-382, vol. 26, No. 3.
D'Souza-Schorey Crislyn et al., ARF Proteins: Roles in Membrane Traffic and Beyond, Nature Reviews Molecular Cell Biology, pp. 347-358, vol. 7, No. 5, Nature Publishing, GB.
PCT International Search Report, PCT/EP2010/069000, dated Mar. 22, 2011.

* cited by examiner

*Primary Examiner* — Ralph Gitomer
(74) *Attorney, Agent, or Firm* — TraskBritt, P.C.

(57) ABSTRACT

The invention relates to the field of disorders of the peripheral or central nervous system, in particular, Alzheimer's disease, and the prevention and/or treatment thereof. In particular, the invention relates to ARF6 and/or ARF6 effector proteins as new targets in Alzheimer's disease, and based thereon, screening methods for compounds that reduce amyloid beta peptide formation in mammalian cells by affecting ARF6-mediated endosomal sorting.

10 Claims, 11 Drawing Sheets

SCREENING METHODS FOR COMPOUNDS THAT MODULATE ARF-6 MEDIATED ENDOSOMAL REDISTRIBUTION

CROSS-REFERENCE TO RELATED APPLICATIONS

This is a national phase entry under 35 U.S.C. §371 of International Patent Application PCT/EP2010/069000, filed Dec. 6, 2010, published in English as International Patent Publication WO 2011/067420 A1 on Jun. 9, 2011, which claims the benefit under Article 8 of the Patent Cooperation Treaty and 35 U.S.C. §119(e) to U.S. Provisional Patent Application Ser. No. 61/283,476, filed Dec. 4, 2009.

TECHNICAL FIELD

The invention relates generally to biotechnology and medicine and, more specifically, to the field of disorders of the peripheral or central nervous system, in particular, Alzheimer's disease, and the prevention and/or treatment thereof. In particular, the invention relates to ARF6 and/or ARF6 effector proteins as new targets in Alzheimer's disease, and (based thereon) screening methods for compounds that reduce amyloid beta peptide formation in mammalian cells. The invention also relates to inhibiting and/or activating agents targeting ARF6 and pharmaceutical compositions thereof, and their use in therapeutic applications of the disorders. The invention also relates to restoring dysfunction in endosomal sorting and degradation seen as a very early pathological feature in Alzheimer's disease. The invention also relates to a cell line and the use thereof for identifying compounds blocking ARF6-mediated endosomal sorting.

BACKGROUND

Alzheimer's disease (AD) is the most common neurodegenerative disorder afflicting the elderly. AD is clinically characterized by progressive neuronal loss and inflammation, memory impairment, cognitive deficits, and behavioral changes. Neuropathologically, the AD brain is characterized by two proteinaceous aggregates, amyloid plaques, mainly composed of the amyloid β-protein (Aβ), and neurofibrillary tangles (NFT), comprised of hyperphosphorylated aggregates of the tau protein (Selkoe 2001). Two major hypotheses have driven pharmaceutical research in the search for a medication for AD: the amyloid hypothesis (Hardy and Selkoe 2002) and the cholinergic hypothesis (Bartus et al. 1982). Although significant progress has been made toward understanding the pathophysiology of AD, significant questions remain unanswered, e.g., the potential link between amyloid pathology and the cholinergic deficit observed in AD patients and the relationship between Aβ generation, neuronal cell death, and NFTs.

Aβ is derived from proteolysis of the β-amyloid precursor protein (APP), a type I integral membrane protein, following sequential cleavage by the β-(BACE1) and γ-secretases. The γ-secretase is a tetrameric complex that cleaves APP within its transmembrane domain, thereby liberating the intact Aβ peptide, which ranges in length from 39-43 residues (De Strooper et al. 2003). The majority of Aβ produced is 40 amino acids in length ($A\beta_{40}$), whereas a small proportion (~10%) is the 42-residue variant ($A\beta_{42}$). $A\beta_{42}$ is more hydrophobic, aggregates much faster than $A\beta_{40}$, is more toxic than $A\beta_{40}$, and is the major Aβ species found in cerebral plaques (Selkoe 2001; Iwatsubo 1994).

Despite intensive research during the last 100 years, prognosis of AD patients now is still quite the same as that of patients a century ago, since there is still no real cure available. There are two types of drugs approved by the U.S. Food and Drug Administration and used in clinics today to treat AD: Acetylcholinesterase (AchE) inhibitors and Memantine. There is ample evidence in the art that the amyloid beta peptide, the main component of the amyloid plaques that are specific to the AD etiology, has a key role in the development of AD disease (Hardy et al. 2002; Golde et al. 2006). Therefore, one of the most common strategies to lower Aβ is to diminish its production by γ- and β-secretase inhibition. One strategy was the development of gamma-secretase inhibitors; however, such inhibitors often result in serious side effects since gamma-secretase is involved in the proteolytic processing of at least 30 proteins (De Strooper et al. 2003). Yet another attractive strategy is the development of β-secretase (BACE1) inhibitors, as BACE1 knock-out mice are viable and have no obvious pathological phenotype (e.g., Roberds et al. 2001; Ohno et al. 2004; Ohno et al. 2006).

SUMMARY OF THE INVENTION

There is increasing evidence that endosomes constitute a major site where Aβ peptides are produced. Aβ peptide, the primary constituents of senile plaques, which are a hallmark in the pathology of Alzheimer's disease, is generated by the sequential cleavage of the amyloid precursor protein (APP) by BACE1 and γ-secretase. Understanding BACE1 intracellular sorting and trafficking is of major importance for the development of therapeutic inhibition of Aβ production as it is the enzyme responsible for the generation of this peptide.

Surprisingly, it was found that BACE1 enters the cell via a distinct route than APP; more specifically, BACE1 enters the cells via a clathrin-independent ARF6-mediated pathway before reaching the Rab5-positive endosome, whereas APP is internalized via a clathrin-dependent pathway. ARF6 is a small GTPase that regulates the trafficking of endosomal membrane (D'Souza-Schorey and Schavrier 2006). It was found that ARF6 cycling activity influences the processing of APP. It was demonstrated that blocking BACE1 in the ARF6 vacuoles prevents BACE1 reaching the Rab5-positive endosomes and thereby prevents processing of APP, supporting that shedding of APP occurs in the endosomal compartments. These findings highlight the importance of the (early) endosomal compartment as the major site of BACE1 processing and open novel avenues for interfering with Aβ production through selectively interfering with the distinct internalization and endosomal recycling routes.

Therefore, the invention relates to ARF6 and/or ARF6 effector proteins as new targets in Alzheimer's disease, since it was surprisingly found that by modulating the activity of ARF6, the formation of amyloid beta peptides in mammalian cells can be significantly reduced.

Disclosed is a method for reducing amyloid beta peptide formation in a mammalian cell comprising modulating the ARF6 cycling activity and/or ARF6 effector protein activity. Accordingly, the invention relates to the use of ARF6 and/or an ARF6 effector to reduce amyloid beta peptide formation in a mammalian cell.

Disclosed is a method for identifying compounds that reduce amyloid beta peptide formation in a mammalian cell comprising modulating the ARF6 cycling activity and/or ARF6 effector activity. Accordingly, the invention relates to the use of ARF6 and/or an ARF6 effector to identify compounds that reduce amyloid beta peptide formation in a mammalian cell.

In another aspect, the invention relates to an agent such as an antisense polynucleotide, a ribozyme, or a small interfering RNA (siRNA), characterized in that it reduces amyloid beta peptide formation, and wherein the agent comprises a nucleic acid molecular sequence complementary to, or engineered from, an ARF6 encoding polynucleotide.

In still another aspect, the invention relates to a pharmaceutical composition comprising a therapeutically effective amount of any of the above-described agents and at least one of a pharmaceutically acceptable carrier, adjuvant or diluents.

Also described is a cell line characterized by lacking endogenous presenilin expression or function (PSENdKO cell line) and the same cell line stably expresses virally transduced ARF6.

In particular, the PSENdKO cell line and the PSENdKO cell line expressing ARF6 can be used in an assay for screening compounds that are capable of modulating ARF6 protein activity in a mammalian cell. Preferably, the compounds are capable of reducing amyloid beta peptide formation in a mammalian cell. Even more preferably, the compounds are therapeutic candidates for the prevention and/or treatment of a disorder of the peripheral or central nervous system, in particular, Alzheimer's disease. In particular, the cell lines are MEF cell lines.

A particular embodiment of the invention relates to a method for identifying a compound that modulates the endosomal redistribution in a mammalian cell based on the imaging of one or more morphological parameters of cells from a cell suspension culture of the above-described PSENdKO cell line in the presence of a compound and comparing, under the same conditions, to the same morphological parameter(s) of cells of the corresponding wild-type and/or PSENdKO cell line expressing ARF6.

BRIEF DESCRIPTION OF THE DRAWINGS

FIG. 11: Retroviral expression of ARF6 in PSEN1&2dKO MEFs reduces wound healing significantly. (A) A scratch assay was performed on gelatin-coated surfaces under serum-free conditions. Cells were stained with 1 µM calcein-AM for one hour before pictures were taken, either immediately after scratching or 15 hours later. (B) The percentage of the healed wounds was quantified for WT, PSEN1&2dKO, and retrovirally infected PSEN1&2dKO MEFs. Rescue was performed using retroviral transduction of human ARF6 WT-HA and ARF6 T157A-HA constructs. (N=3; means±SEM; * $P<0.05$,  $P<0.01$, * $P<0.005$).

FIG. 12: ARF6 is involved in the decreased turnover of degradative vacuoles in PSEN1&2dKO MEFs. PSEN deficiency leads to the overall accumulation of lysotracker-positive vesicles representing late endosomes or lysosomes. These acidic compartments are accompanied by the accumulation of EGFR in PSEN1&2dKO MEFs as shown by a co-distribution with lysotracker and anti-Lamp 1. PSEN1&2dKO MEFs retrovirally transduced with human ARF6 WT-HA induce the clearance of these acidified organelles, together with an increased degradation of EGFR, resulting in much lower anti-EGFR fluorescence intensity.

FIG. 13: Morphology screen assay.

FIG. 14: Endogenous ARF6 levels decrease with aging. Cortices from mice with ages ranging from prenatal E14 to postnatal 24 months were dissected out, homogenized and extracted in Tris-EDTA buffer (pH 7.3) containing 250 mM sucrose, 1% TritonX-100 and protease inhibitors. Protein concentration of cleared extracts was measured and equal amounts of protein (20 µg) were loaded on pre-cast 4-12% MES SDS-PAGE gels (Invitrogen) and, following electrophoresis, transferred on a nitrocellulose membrane (protran). These blots were blocked and subsequently probed for RAB5, ARF6 and presenilin 1 (PS1) using appropriate primary antibodies. Immunodetection was performed with HRP-conjugated secondary antibodies followed by ECL. Quantitative Western blotting was performed on a FujiLas Mini (acquisition) and data were processed using Lais software (Fuji). Protein concentration and GAPDH were used for normalization between the different experiments. Mean±SEM of two to three independent experiments is shown.

FIG. 15: ARF6 levels are down-regulated in the brain of Alzheimer's disease (AD) patients. Samples of the frontal cortex of human control (18) and AD (47) brains were extracted in Tris-EDTA buffer (pH 7.3) containing 250 mM sucrose, 1% Triton X-100 and protease inhibitors. After measuring protein concentration, equal protein amounts (30 µg) of cleared extracts were processed for SDS-PAGE and Western blotting. Blots were probed for RAB5, ARF6 and GGA3 using the appropriate primary antibodies and quantified. GAPDH was used for normalization. No statistical differences were found for RAB5 between control and AD brain. In the contrary, in AD brain, ARF6 and GGA3 levels dropped 42% and 28%, respectively, compared to control brain.

DETAILED DESCRIPTION

Figure 1:
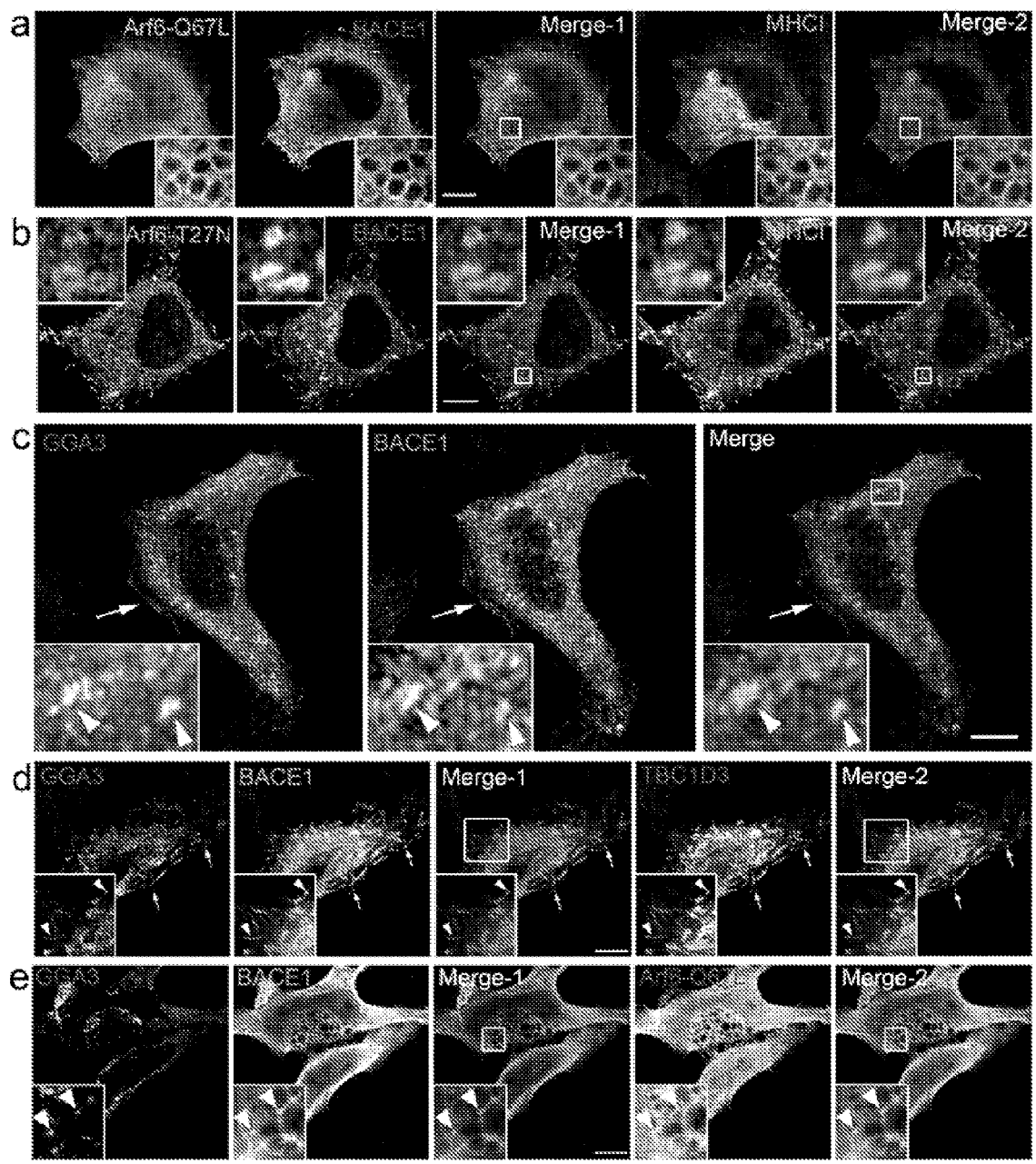
FIG. 1: (a, b) BACE1 localize to ARF6-positive membrane. HeLa cells co-transfected with BACE1 and HA-ARF6-Q67L (a) or HA-ARF6-T27N (b) were fixed and stained for HA, BACE1 and MHCI. (c-e) BACE1 localized with the ARF6-TBC1D3-GGA3 complex at the cell surface. (c) HeLa cells transfected with either (c) FLAG-tagged GGA3 and BACE1, or (d) FLAG-tagged-GGA3, BACE1 and HA-TBC1D3, or (e) FLAG-GGA3, BACE1 and HA- ARF6-Q67L, were fixed and stained for the tags FLAG and HA, and BACE1 as required. (c) Arrow indicates co-localization of GGA3 and BACE1 at the plasma membrane, in the inset, arrowheads indicate co-localization in the endosomal compartment. (d) Arrows indicate co-localization of BACE1 with GGA3 and TBC1D3. (a-e) Magnifications of selected areas, indicated by a square, are shown in insets; arrowheads highlight co-localization. To facilitate visualization, black and white picture for each channel and pseudo colors, as well as two merges if three channels, were used. Bars=10 µm.

A first aspect of the disclosure relates to a method for reducing amyloid beta peptide formation in a mammalian cell comprising modulating the ARF6 cycling activity and/or ARF6 effector protein activity. Accordingly, the invention relates to the use of ARF6 and/or an ARF6 effector to reduce amyloid beta peptide formation in a mammalian cell.

A second aspect of the disclosure relates to a method for identifying compounds that reduce amyloid beta peptide formation in a mammalian cell comprising modulating the ARF6 cycling activity and/or ARF6 effector activity. Accordingly, the invention relates to, among other things, the use of ARF6 and/or an ARF6 effector to identify compounds that reduce amyloid beta peptide formation in a mammalian cell.

The terms "amyloid beta peptide" or "amyloid beta protein" or "Aβ peptide" or "Aβ" are interchangeably used further herein. Amyloid beta peptides are processed from the amyloid beta precursor protein (APP) and include the amyloid beta peptides 1-42, 1-40, 11-42, 11-40, which can ultimately be found in plaques and are often seen in cerebral spinal fluid.

The terms "modulating," "modulation," "modulated" means an up-regulation or down-regulation of the expression, or an increase or decrease in activity of a protein. Modulation of a protein includes the up-regulation, down-regulation, increase or decrease in activity of a protein or compound that regulates a protein. Modulation also includes the regulation of a gene, the mRNA, or any other step in the synthesis of the protein of interest.

The terms "protein," "polypeptide," "peptide" are interchangeably used further herein.

The ADP-ribosylation factor (ARF) family of proteins belongs to the Ras superfamily of small GTPases that regulate vesicular trafficking and organelle structure by recruiting coat proteins, regulating phospholipid metabolism and modulating the structure of actin at membrane surfaces. ARF1 and ARF6, two of the best characterized ARF proteins, provide a molecular context for ARF protein function in fundamental biological processes, such as secretion, endocytosis, phagocytosis, cytokinesis, cell adhesion and tumor-cell invasion (D'Souza-Schorey and Schavrier 2006). Like other Ras-related GTP binding proteins, the ARF proteins cycle between their active-GTP-bound and inactive-GDP-bound conformations. Hydrolysis of bound GTP is mediated by GTPase-activating proteins (GAPs), whereas the exchange of GDP for tri-phosphate nucleotide is mediated by guanine nucleotide-exchange factors (GEFs). Several ARF-specific GEFs and GAPs that interact with one or more ARF proteins have been identified in vitro; however, distinct GAPs and GEFs regulate GTP-GDP cycle of individual ARF proteins in vivo (Jackson and Casanova, 2000; Randazzo et al. 2004). The ARF proteins are ubiquitously expressed and the amino-acid sequences seem to be well conserved in all eukaryotes, from yeast to humans, with remarkable fidelity.

ARF6 is the least conserved member of the ARF family of proteins and shares only 66% amino acid identity with Arf1. ARF6 regulates the trafficking of endosomal membrane and structural organization at the cell surface. The polynucleotide and amino acid sequence of the human ARF6 protein are accessible in public databases by accession numbers CR541939 and CAG46737, respectively. The ARF6 protein as referred to in the disclosure also includes homologues as well as active fragments of the full-length ARF6 polypeptide. "Active," with respect to the ARF6 polypeptide, refers to those forms, fragments or domains of an ARF6 polypeptide which retain the biological and/or antigenic activity of an ARF6 polypeptide.

The term "ARF6 cycling" as used herein means the ARF6 cycling between its active-GTP-bound and inactive-GDP-bound state. The term "ARF6 effector protein" in the context of the disclosure means any protein that directly or indirectly interacts with ARF6 or that intervenes in the ARF6 endocytotic pathway, either upstream or downstream of the ARF6 signaling pathway.

In a particular embodiment of any of the above methods, the ARF6 effector is chosen from a GAP, such as GIT-1, GIT-2, Centaurin α or a GEF, such as EFA6A, EFA6C, EFA6D, ARNO, msec7-1, GRP1, ARF-GEP100 (Jaworski 2007). Preferably, the GAPs and GEFs are predominantly expressed in the nervous system. Other effectors linked to the ARF6 pathway include, but are not limited to, phospholipase D2 (PLD2), PI(4)P5-kinase, other GTPases such as Ras or Rac, Jun N-terminal kinase interacting protein 3 and −4 (JIP3 and 4), and other Rabs such as Rab 11, Rab22A, Rab 10, Rab35 (reviewed in D'Souza-Schorey and Chavrier 2006). ARF6 functioning at the cell surface can be mediated by its effect on phospholipid metabolism. In this regard, ARF6 activates phospholipase D2 (PLD2) leading to the formation of lysophosphatic acid and diacylglycerol, which are important for endosomal recycling via this route. ARF6 also activates PI(4)P5-kinase, generating PI(4,5)P2 with a similar function as above. ARF6 is also activated via activation of the ERK pathway or via activities of other GPTases such as Ras or Rac. ARF6 also binds to Jun N-terminal kinase interacting protein 3 and −4 (JIP3 and 4) for targeting the recycling endosomal membrane to the cell surface. Other Rabs that interfere in this route are Rab11, Rab22A, Rab10, Rab35.

The term "compound" is used herein in the context of a "test compound" or a "drug candidate compound" described in connection with the methods of the disclosure. As such, these compounds comprise organic or inorganic compounds, derived synthetically or from natural resources. The compounds include polynucleotides, lipids or hormone analogs that are characterized by low molecular weights. Other biopolymeric organic test compounds include small peptides or peptide-like molecules (peptidomimetics) comprising from about 2 to about 40 amino acids and larger polypeptides comprising from about 40 to about 500 amino acids, such as antibodies or antibody conjugates.

Examples of assay methods for identifying compounds in the context of the disclosure are described in the Example section, without the purpose of being limitative. It should be clear to the skilled artisan that the present screening methods might be based on a combination or a series of measurements, particularly when establishing the link with amyloid beta peptide generation. Also, it should be clear that there is no specific order in performing these measurements while practicing the invention.

For high-throughput purposes, compound libraries may be used. Examples include, but are not limited to, natural compound libraries, allosteric compound libraries, peptide libraries, antibody fragment libraries, synthetic compound libraries, etc.

Determining the level of amyloid beta peptides produced can be done by using specific ELISAs using antibodies specifically recognizing the different amyloid beta peptide species or by identifying amyloid beta peptides and other APP processing products (APP-carboxyteiminal fragments, ectodomains) following metabolic labeling. A reduction in the level of amyloid beta peptides formed is preferably by at least 5%, more preferably by at least 10%, and most preferably by at least 25%, 50% or more.

Assays can be performed in eukaryotic cells, advantageously in mammalian cells, such as human cells. Appropriate assays can also be performed in prokaryotic cells, reconstituted membranes, and using purified proteins in vitro.

Polypeptide therapeutics and, in particular, antibody-based therapeutics have significant potential as drugs because they have exquisite specificity to their target and a low inherent toxicity. In particular, the features of monoclonal antibodies such as high affinity, high selectivity, and distinct structure and function domains amenable to protein engineering for therapeutic delivery, make them potential drug candidates. Given the growing potential for the utilization of monoclonal antibodies as therapeutics, GPR3-specific monoclonal antibodies can be generated using techniques well known by the skilled person as these form part of the current state of the art and the effectiveness of these antibodies as modulators of Aβ generation can also be determined in the context of the invention.

Active fragments of the above-described antibodies also form part of the invention. The term "active fragment" refers to a portion of an antibody that by itself has high affinity for an antigenic determinant, or epitope, and contains one or more CDRs accounting for such specificity. Non-limiting examples include Fab, F(ab)'2, scFv, heavy-light chain dinners, nanobodies, domain antibodies, and single chain structures, such as a complete light chain or complete heavy chain.

The antibodies of the invention, or their active fragments, can be labeled by an appropriate label, the label can, for instance, be of the enzymatic, colorimetric, chemiluminescent, fluorescent, or radioactive type.

It is known by the skilled person that an antibody that has been obtained for a therapeutically useful target requires additional modification in order to prepare it for human therapy, so as to avoid an unwanted immunological reaction in a human individual upon administration. The modification process is commonly termed "humanization". It is known by the skilled artisan that antibodies raised in species, other than in humans, require humanization to render the antibody therapeutically useful in humans ((1) CDR grafting: Protein Design Labs: U.S. Pat. No. 6,180,370, U.S. Pat. No. 5,693,761; Genentech U.S. Pat. No. 6,054,297; Celltech: EP626390, U.S. Pat. No. 5,859,205; (2) Veneering: Xoma: U.S. Pat. No. 5,869,619, U.S. Pat. No. 5,766,886, U.S. Pat. No. 5,821,123). Humanization of antibodies entails recombinant DNA technology, and is departing from parts of rodent and/or human genomic DNA sequences coding for H and L chains or from cDNA clones coding for H and L chains. Techniques for humanization of non-human antibodies are known to the skilled person as these form part of the current state of the art. Non-human mammalian antibodies or animal antibodies can be humanized (see, for instance, Winter and Harris 1993). The antibodies or monoclonal antibodies according to the invention may be humanized versions of, for instance, rodent antibodies or rodent monoclonal antibodies.

The use of ARF6 and/or an ARF6 effector to reduce amyloid beta peptide generation in a mammalian cell is also envisioned in the disclosure, as well as the use of ARF6 and/or an ARF6 effector to identify compounds that reduce amyloid beta peptide formation in a mammalian cell. In one embodiment, the ARF6 and/or the ARF6 effector can be a mutant or can be over-expressed or can be down-regulated. Examples of ARF6 mutants are known in the art, e.g., ARF6-Q67L, which is a dominant active mutant locking ARF6 in its GTP bound state or ARF6-T27N, which is a GDP-locked inactive ARF6 (Peters et al. 1995). Other non-limiting examples of how ARF6 and/or ARF6 effectors can be mutated, over-expressed or down-regulated are described in the Example section.

In a further aspect, also disclosed is the use of ARF6 and/or an ARF6 effector to diagnose or prognose Alzheimer's disease. The "use" as meant herein is any use of the nucleic acid or protein, and may be, as a non-limiting example, the genomic DNA, for the detection of mutation, the mRNA or derived cDNA, for the analysis of the expression, or the protein, for the analysis of translated protein. Methods for mutation and SNP analysis, expression analysis and detection and quantification of protein (e.g., via antibodies recognizing the protein) are known to the person skilled in the art.

In still another aspect, the disclosure relates to an agent such as an antisense polynucleotide, a ribozyme, or a small interfering RNA (siRNA), characterized in that it is reducing amyloid beta peptide formation, and wherein the agent comprises a nucleic acid sequence complementary to, or engineered from, an ARF6 encoding polynucleotide.

The terms "polynucleotide," "polynucleic acid," and "nucleic acid" are interchangeably used further herein.

In a preferred embodiment, the agents of the invention encompass short interfering RNA (siRNA) molecules that down-regulate expression of ARF6 mRNA by RNA interference. RNA interference refers to the process of sequence-specific post-transcriptional gene silencing in animals mediated by short interfering RNAs (siRNA) (Fire et al. 1998). siRNA molecules are short pieces of dsRNA obtained by processing of the dsRNA by Dicer, a ribonuclease III enzyme (Bernstein et al. 2001). Short interfering RNAs derived from Dicer activity are typically about 21-23 nucleotides in length and comprise about 19 base pair duplexes. siRNAs up to 26 nucleotides have proven to be effective at specifically silencing gene expression without causing any interferon response. The siRNA molecules of the disclosure encompass human ARF6 siRNAs, which are useful for research to analyze the function of ARF6, and which may be used for therapy in humans, e.g., in the prevention and/or treatment of a disorder of the peripheral or central nervous system, in particular, Alzheimer's disease. In a specific embodiment, the small interfering RNAs (siRNA) of the disclosure comprise a nucleic acid sequence as defined by SEQ ID NOS:1 and 2 (Table 1).

TABLE 1

| Specific siRNAs for ARF6 | | |
|---|---|---|
| Gene | Full sequence siRNA (sense strand) | SEQ ID NO: |
| ARF6 | 5'-GCACCGCATTATCAATGACCG-3' | 1 |
| ARF6 | 5'-GGTCTCATCTTCGTAGTGG-3' | 2 |

Based on the RNA sequence of human ARF6, siRNA molecules with the ability to knock-down ARF6 activity can be obtained by chemical synthesis or by hairpin siRNA expression vectors (as described by Yu et al. 2002). There are numerous companies that provide the supply of customer-designed siRNAs on a given RNA sequence, e.g., Ambion, Imgenex, Dharmacon.

The ARF6 siRNAs of the invention may be chemically modified, e.g., as described in US20030143732, by phosphorothioate internucleotide linkages, 2'-O-methyl ribonucleotides, 2'-deoxy-2'fluoro ribonucleotides, "universal base" nucleotides, 5-C-methyl nucleotides, and inverted deoxyabasic residue incorporation. The sense strand of ARF6 siRNAs may also be conjugated to small molecules or peptides, such as membrane-permeant peptides or polyethylene glycol (PEG). Other siRNA conjugates that form part of the disclosure include cholesterol and alternative lipid-like molecules, such as fatty acids or bile-salt derivatives.

In a further embodiment, the disclosure relates to an expression vector comprising any of the above-described polynucleotide sequences encoding at least one ARF6 siRNA molecule in a manner that allows expression of the nucleic acid molecule, and cells containing such vector. The polynucleic acid sequence is operably linked to regulatory signals (promoters, enhancers, suppressors, etc.), enabling expression of the polynucleic acid sequence and is introduced into a cell utilizing, preferably, recombinant vector constructs. A variety of viral-based systems are available, including adenoviral, retroviral, adeno-associated viral, lentiviral, herpes simplex viral vector systems. Selection of the appropriate viral vector system, regulatory regions and host cell is common knowledge within the level of ordinary skill in the art.

As gene delivery and gene silencing techniques improve, the selective deletion of ARF6 in particular tissues or cellular populations may prove useful in order to limit the impact of protein deletion to a particular system under study. The ARF6 siRNA molecules of the invention may be delivered by known gene delivery methods, e.g., as described in US 20030143732, including the use of naked siRNA, synthetic nanoparticles composed of cationic lipid formulations, liposome formulations including pH-sensitive liposomes and immunoliposomes, or bioconjugates including siRNAs conjugated to fusogenic peptides. Delivery of siRNA expressing vectors can be systemic, such as by intravenous or intramuscular administration or by any other means that would allow for introduction into the desired target cell (see US 20030143732).

In still another aspect, also described is a pharmaceutical composition comprising a therapeutically effective amount of any of the above-described agents and at least one of a pharmaceutically acceptable carrier, adjuvant or diluents. Any of the above agents or the pharmaceutical composition can be used for the manufacture of a medicament to prevent and/or treat a disorder of the peripheral or central nervous system, in particular Alzheimer's disease. One of ordinary skill in the art will recognize that the potency and, therefore, an "effective amount" can vary for the inhibitory agents of the invention. One skilled in the art can readily assess the potency of the inhibitory agent.

A medicament to prevent and/or to treat a disorder of the peripheral or central nervous system, in particular, Alzheimer's disease, relates to a composition comprising agents as described above and a pharmaceutically acceptable carrier or excipient (both terms can be used interchangeably) to treat or to prevent diseases as described herein.

The administration of pharmaceutical compositions may be by way of oral, inhaled or parenteral administration. In particular, pharmaceutical compositions can be delivered through intrathecal or intracerebroventricular administration. The active ingredient may be administered alone or preferably formulated as a pharmaceutical composition. An amount effective to treat Alzheimer's disease depends on the usual factors such as the nature and severity of the disorder being treated and the weight of the mammal. It is greatly preferred that the pharmaceutical composition is administered in the form of a unit-dose composition, such as a unit dose oral, parenteral, or inhaled composition. Such compositions are prepared by admixture and are suitably adapted for oral, inhaled or parenteral administration, and as such, may be in the form of tablets, capsules, oral liquid preparations, powders, granules, lozenges, reconstitutable powders, injectable and infusable solutions or suspensions or suppositories or aerosols. Tablets and capsules for oral administration are usually presented in a unit dose, and contain conventional excipients such as binding agents, fillers, diluents, tabletting agents, lubricants, disintegrants, colorants, flavorings, and wetting agents. The tablets may be coated according to well-known methods in the art. Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate. These solid oral compositions may be prepared by conventional methods of blending, filling, tabletting or the like. Repeated blending operations may be used to distribute the active agent throughout those compositions employing large quantities of fillers. Such operations are, of course, conventional in the art. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example, sorbitol, syrup, methyl cellulose, gelatin, hydroxyethylcellulose, carboxymethyl cellulose, aluminum stearate gel or hydrogenated edible fats, emulsifying agents, for example, lecithin, sorbitan monooleate, or acacia; non-aqueous vehicles (which may include edible oils), for example, almond oil, fractionated coconut oil, oily esters such as esters of glycerin, propylene glycol, or ethyl alcohol; preservatives, for example, methyl or propyl p-hydroxybenzoate or sorbic acid, and if desired conventional flavoring or coloring agents. Oral formulations also include conventional sustained release formulations, such as tablets or granules having an enteric coating. Preferably, compositions for inhalation are presented for administration to the respiratory tract as a snuff or an aerosol or solution for a nebulizer, or as a microfine powder for insufflation, alone or in combination with an inert carrier such as lactose. In such a case, the particles of the active compound suitably have diameters of less than 50 microns, preferably less than 10 microns, for example, between 1 and 5 microns, such as between 2 and 5 microns. For parenteral administration, fluid unit dose forms are prepared containing a compound of the invention and a sterile vehicle. The active compound, depending on the vehicle and the concentration, can be either suspended or dissolved. Parenteral solutions are normally prepared by dissolving the compound in a vehicle and filter sterilizing before filling into a suitable vial or ampoule and sealing. Advantageously, adjuvants such as a local anesthetic, preservatives and buffering agents are also dissolved in the vehicle. To enhance the stability, the composition can be frozen after filling into the vial and the water removed under vacuum. Parenteral suspensions are prepared in substantially the same manner except that the compound is suspended in the vehicle instead of being dissolved and sterilized by exposure to ethylene oxide before suspending in the sterile vehicle. Advantageously, a surfactant or wetting agent is included in the composition to facilitate uniform distribution of the active compound. Where appropriate, small amounts of bronchodilators, for example, sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included. As is common practice, the compositions will usually be accompanied by written or printed directions for use in the medical treatment concerned.

The terms "therapeutically effective amount," "therapeutically effective dose" and "effective amount" mean the amount needed to achieve the desired result or results (modulating ARF6 activity; treating or preventing Alzheimer's disease).

"Pharmaceutically acceptable" means a material that is not biologically or otherwise undesirable, i.e., the material may be administered to an individual along with the compound without causing any undesirable biological effects or interacting in a deleterious manner with any of the other components of the pharmaceutical composition in which it is contained.

A "carrier" or "adjuvant," in particular, a "pharmaceutically acceptable carrier" or "pharmaceutically acceptable adjuvant," is any suitable excipient, diluent, carrier and/or adjuvant that, by themselves, do not induce the production of antibodies harmful to the individual receiving the composition nor do they elicit protection. Preferably, a pharmaceutically acceptable carrier or adjuvant enhances the immune response elicited by an antigen. Suitable carriers or adjuvantia typically comprise one or more of the compounds included in the following non-exhaustive list: large slowly metabolized macromolecules such as proteins, polysaccharides, polylactic acids, polyglycolic acids, polymeric amino acids, amino acid copolymers and inactive virus particles.

A "diluent," in particular, a "pharmaceutically acceptable vehicle," includes vehicles such as water, saline, physiological salt solutions, glycerol, ethanol, etc. Auxiliary substances such as wetting or emulsifying agents, pH buffering substances, and preservatives may be included in such vehicles.

It should be clear that the inhibitory agents of the invention for Alzheimer's disease can also be used in combination with any other AD disease therapy known in the art such as gamma-secretase inhibitors or beta-secretase inhibitors.

A further aspect of the invention relates to a cell line characterized by lacking endogenous presenilin expression or function and the same cell line stably expressing virally transduced ARF6 (see Example 3). Presenilins (PS, PSEN) have been shown to form the catalytic subunit of the γ-secretase complex that produces the Aβ peptide. So, a PSEN double knockout cell line (PSENdKO), lacking endogenous presenilin expression (PSEN1 and PSEN2), lacks γ-secretase activity. However, despite the γ-secretase-dependent (catalytical) function, presenilins also have other functions, such as a role in trafficking of membrane proteins. So, a PSENdKO cell line has an aberrant morphological phenotype due to typical endosomal trafficking defects, such as aberrant accumulation of membrane lipids and proteins. It was shown in the invention that by "rescuing" the PSENdKO cell line with the ARF6 GTPase, the aberrant morphological phenotype observed in the PSENdKO cell line could be restored. Therefore, the "rescue" cell line allows discrimination between the γ-secretase independent versus γ-secretase dependent (catalytical) function and, as such, is a valuable screening tool for new drug compounds. In particular, the PSENdKO cell line and the PSENdKO cell line expressing ARF6 can be used in an assay for screening compounds that are capable of modulating ARF6 protein activity in a mammalian cell. Preferably, the compounds are capable of reducing amyloid beta peptide formation in a mammalian cell. Even more preferably, the compounds are therapeutic candidates for the prevention and/or treatment of a disorder of the peripheral or central nervous system, in particular, Alzheimer's disease. In particular, the cell lines are MEF cell lines.

A particular embodiment of the invention relates to a method for identifying compounds that modulate the endosomal redistribution in a mammalian cell comprising the steps of:
a) providing a cell culture characterized by lacking endogenous presenilin expression/function;
b) administering a test compound to the cell culture; and
c) imaging at least one morphological parameter of the cells in the cell culture;
wherein, under the same test conditions, a deviation or aberration in the at least one parameter compared to the same at least one parameter of cells of a corresponding wild-type cell culture and/or of the cell culture characterized by lacking endogenous presenilin expression/function stably expressing ARF6, identifies the test compound as a compound that modulates the endosomal redistribution in a mammalian cell.

The term "morphological parameters" in the context of the invention includes, but is not limited to, cell area, cell perimeter, cell ratio area/perimeter, cell elongation, cell diameter, cell intensity, cell count, cell roundness. Differences in morphological phenotype between cell cultures in the presence of test compounds can be screened in a high-throughput imaging setup (e.g., InCell 2000, GE Healthcare; see also Example 4).

The phrase "modulate (or modulation or modulating) of the endosomal redistribution" as used herein refers to interfering with the activity of the endocytic pathway, wherein the activity includes, but is not limited to: (i) endocytic rates; (ii) endosomal fusion and recycling; (iii) degree of accumulation of lipid species such as cholesterol and sphingomyelins and/or proteins or enzymes; (iv) degree of accumulation of β-amyloidogenic fragments or aggregated proteins or protein fragments in endosomal compartments; or (v) degree of accumulation of autophagic vacuoles. Usually, an abnormal endocytic pathway is one that exhibits an increase or decrease in one or more of the foregoing activities, in other words, a change in endosomal balance that is aberrant from the normal situation. In a preferred embodiment, a compound will "decrease" or "reduce" the abnormal activity of the endocytic pathway. The reduction is preferably by at least 5%, more preferably by at least 10%, and most preferably by at least 25%, 50% or more. Assays and methods for measuring the activity of the endocytic pathway are known in the art. As a non-limiting example, filipin can be administered to the above-mentioned cell cultures to identify cholesterol accumulations as a readout for endosomal accumulations.

In a more specific embodiment, the compound modulates ARF6 cycling activity and/or ARF6 effector protein activity. Preferably, the compound is capable of reducing amyloid beta peptide formation in a mammalian cell and, as such, is a therapeutic candidate for the prevention and/or treatment of Alzheimer's disease. The reduction is preferably by at least 5%, more preferably by at least 10%, and most preferably by at least 25%, 50% or more.

The following examples are intended to promote a further understanding of the disclosure. While the disclosure is described herein with reference to illustrative embodiments, it should be understood that the invention is not limited thereto. Those having ordinary skill in the art and access to the teachings herein will recognize additional modifications and embodiments within the scope thereof. Therefore, the invention is limited only by the associated claims.

EXAMPLES

Example 1

BACE1 Internalizes Via the Clathrin-Independent ARF6-Mediated Endocytotic Pathway The β-amyloid precursor protein (APP) internalizes via a clathrin-dependent pathway (Schneider et al. 2008); however, the molecular machinery involved in the regulation of BACE1 internalization remains unknown. Unlike APP, BACE1 does not contain a sorting motif within its tails, which could regulate its internalization via the clathrin route (Traub 2009). However, BACE1's cytosolic tail (aa 496-500) contains an acid cluster-dileucine motif (ACDL, DISLL sequence) that has been shown to regulate its trafficking between the endosomal compartments as well as its internalization (Capell et al. 2000; Huse and Pijak 2000; Pastorino et al. 2002). The ACDL motif of BACE1 binds to the Golgi-localized gamma-ear containing ADP ribosylation factor-binding (GGA) family (He et al. 2002; Shiba et al. 2004; von Arnim et al. 2004; He et al. 2005; Wahle et al. 2005). These are small monomeric adaptors involved in the transport of protein mostly between the TGN and the endosome and in the recycling pathway from the endosomes to the TGN (Bonifacino 2004; He et al. 2005). All three GGA (1, 2 and 3) appear to be involved in the trafficking of BACE1 as depletion of any of them causes a significant change in the distribution of BACE1 (He et al. 2005). Recently, GGA3 was shown to be recruited by ARF6, a small GTPase involved in membrane trafficking (D'Souza-Schorey and Chavrier 2006; Grant and Donaldson 2009), and TBC1D3, a TBC-containing protein lacking GAP activity, at the plasma membrane and involved in a macropinocytosis route (Frittoli et al. 2008). GGA3 has also been implicated in trafficking and down-regulation of BACE1 (Tesco et al. 2007).

It was investigated whether BACE1 could be a cargo of this ARF6-mediated macropinocytotic pathway by first looking at BACE1 localization in cells over-expressing ARF6 cycle mutants (Peters et al. 1995). We tested this by first co-expressing BACE1 with ARF6-Q67L, a dominant active mutant locking ARF6 in its GTP-bound state (Peters et al. 1995). As shown in FIG. 1, panel a, BACE1 becomes clearly trapped together with ARF6 cargo proteins like MHCI in characteristic grape-like vacuoles (Brown et al. 2001; Naslaysky et al. 2003; Naslaysky et al. 2004). On the other hand, blocking ARF6 activation, by expressing the GDP-locked inactive ARF6, ARF6-T27N mutant, inhibits recycling to the cell surface (Peters et al. 1995). In this condition, BACE1 also co-localized with MHCI trapped in ARF6-T27N-positive recycling endosomal structures (FIG. 1, panel b, inset). In addition, in the case of both mutants, MHCI and BACE1 often co-localized to ARF6-positive protrusions or ruffles at the cell surface (FIG. 1, panels a and b). Alternatively, ARF6 activation through over-expression of its specific guanine nucleotide exchange factor (GEF) EFA6 equally induces protrusions and macropinosomes (Franco et al. 1999), which turned out to be positive for BACE1 when co-over-expressed (data not shown). In addition, both BACE1 and GGA3 co-localized at the cell surface as well as intracellularly (FIG. 1, panel c). It has been shown that TBC1D3 over-expression induce extensive formation of ruffle-like structures at the dorsal surface of the cells, thereby recruiting GGA3 (Frittoli et al. 2008). Indeed, the co-localization of GGA3 with BACE1 was clearly enhanced at TBC1D3-induced ruffles (FIG. 1, panel d, arrows and arrowheads in the inset).

In addition, when co-expressed with ARF6-Q67L, BACE1 and GGA3 became trapped in ARF6-positive vacuoles (FIG. 1, panel e) (Frittoli et al. 2008). These results clearly show that GGA3 likely recruits BACE1 for internalization through the ARF6-dependent macropinocytic uptake route.

In contrast, APP has been shown to require the clathrin-dependent pathway for internalization (Carey et al. 2005; Schneider et al. 2008). Indeed, when APP was co-expressed with ARF6-Q67L, we did not observe APP accumulating in ARF6-positive endocytic vacuoles (FIG. 2, panel a), underscoring that the substrate APP and its sheddase follow distinct internalization routes.

Figure 2:
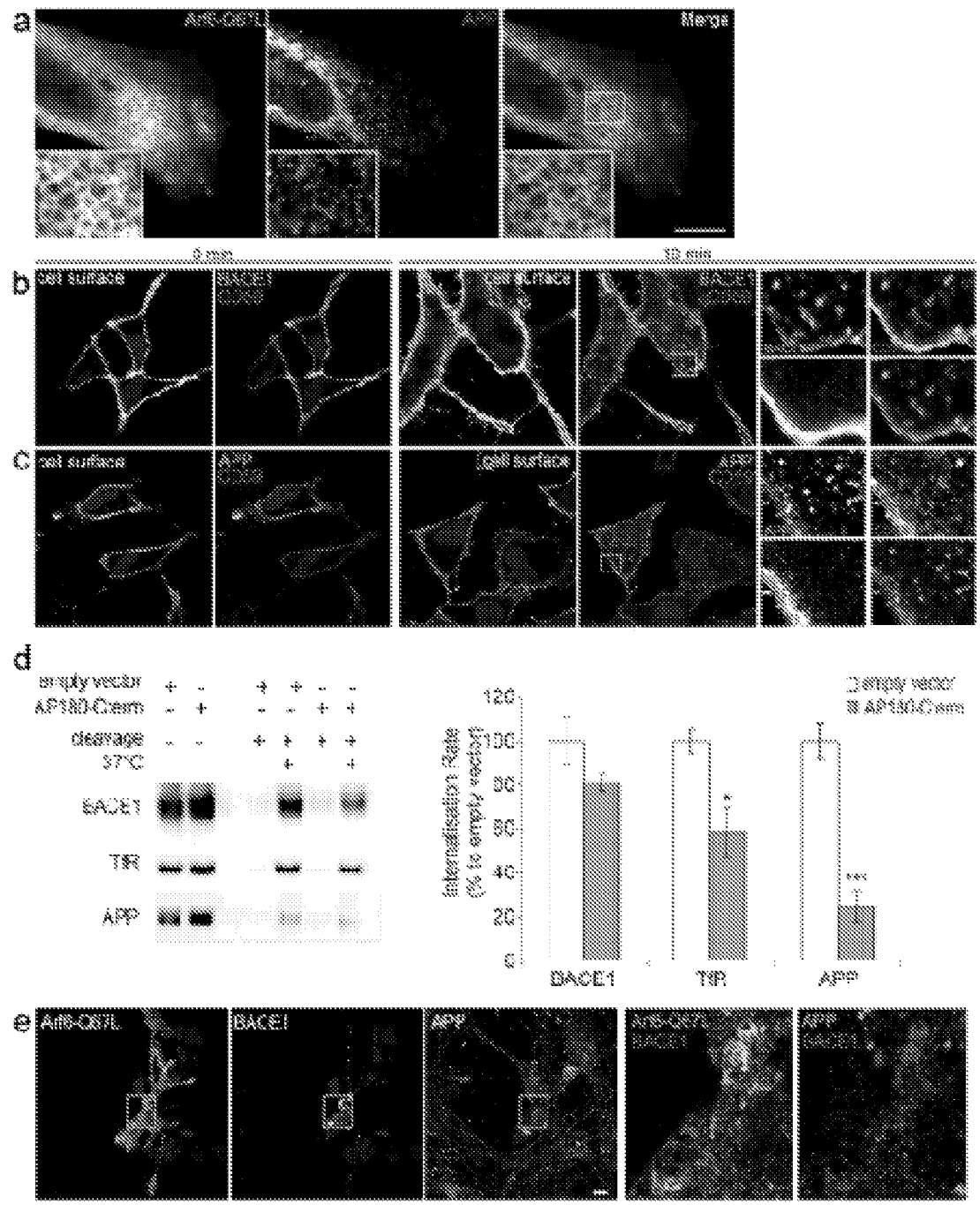
FIG. 2: BACE1, but not APP, internalize via a clathrin-independent pathway. (a) APP endocytosis is not mediated by ARF6. HeLa cells co-transfected with APP and HA-ARF6-Q67L were fixed after 24 hours and stained for the tag HA and APP. Note that APP is clearly absent from the vacuoles created by over-expression of ARF6-Q67L. Magnification of this region is shown in the inset. (b, c) Internalization of BACE1 (b) and APP (c) together with CD59 antibodies were performed in HeLa cells transiently expressing BACE1 or APP accordingly (24 hours). After 10 minutes at 37° C., with EGF (200 ng/ml) stimulation, cells were fixed on ice. Before permeabilization, cells were incubated with pacific blue-labeled secondary antibody to visualize the cell surface, then after permeabilization, 488- and 568-labeled secondary antibodies were used to stain internalized primary antibodies of BACE1 (b) or APP (c) and CD59, respectively. Cells kept on ice (0 minutes) do not show internalization of CD59, BACE1 or APP. Right panels show magnifications of selected. (d) HeLa cells were co-transfected with BACE1 and empty vector or with BACE1 and a truncated form of AP180 (AP180-Cterm). Twenty-four hours later, the cells were labeled with EZ-Link Sulfo-NHS-SS-Biotin at 4° C. for 15 minutes. After washes, the cells were incubated at 37° C. for 10 minutes allowing endocytosis. Remaining biotin at the cell surface was reduced before lysing the cells and internalized biotin were pooled down and detected as indicated in materials and methods. Western blot results of a representative experiment is shown in (d) left panel and quantification of the signal of three independent experiments was generated for BACE1, transferrin receptor (TfR) and APP (d, right panel) (***, $p<0,1\%$). (e) BACE1 is trapped in ARF6-Q67L vacuoles in neuronal cell. Rat hypocampal neurones were co-transfected with ARF6-Q67L and BACE1 six days after plating. Twenty-four hours later, the cells were fixed and stained for tag HA, BACE1 and APP. Two merges are shown on the right-hand side to highlight BACE1 (red) trapped in the ARF6-Q67L (green) vacuoles and that BACE1 (green) and APP do not co-localize in these vacuoles.

To further corroborate these findings, we followed the fate of cell surface localized BACE1 and APP using an antibody uptake assay. Hela cells were incubated at 4° C. with antibodies directed against BACE1 and CD59, a GPI-anchor protein following the ARF6 route, and subsequently chased at 37° C. in the presence of high EGF concentrations (200 ng/ml) to stimulate macropinocytosis (Lanzetti et al. 2004). After 10 minutes, most of the internalized antibody-BACE1 conjugates co-localized with CD59-positive endosomal compartments (FIG. 2, panel b), indicating that the major pool of surface localized BACE1 entered the cell via the ARF6-dependent pathway. On the contrary, in a similar setup, no internalized APP was co-localizing with CD59 (FIG. 2, panel c). Next, it was investigated whether a selective inhibition of the clathrin-dependent pathway would selectively affect APP but not BACE1 internalization. Therefore, BACE1 or APP were over-expressed together with the carboxy-terminal domain of AP180 (AP180-C). AP180 is a nonconventional neuronal adaptor protein of the clathrin pathway that, when truncated, blocks internalization (Zhao 2001; Frittoli et al. 2008). Next, cells were surface biotinylated and following a ten-minute chase, the amount of internalized biotinylated BACE1, APP or endogenous transferrin receptor (TfR) was quantified (FIG. 2, panels c and d). While endocytosis of APP was efficiently inhibited by 80%, as reported (Schneider et al. 2008), BACE1 internalization was only slightly but not significantly affected. Also, another typical clathrin-dependent cargo protein, TfR (Schneider et al. 2008), was inhibited by ~40% (p<5%, FIG. 2, panel d). The lower efficiency here might, however, be due to the fact that TfR is endogenously expressed. Again, our data confirm independently that internalization of BACE1 and APP can be separately controlled. Interestingly, when we transfected primary hippocampal neurons with ARF6-Q67L, over-expressed BACE1 but not APP accumulated in ARF6-positive vacuoles (FIG. 2, panel e), indicating that distinct internalization routes for BACE1 and APP also exist in the brain.

Figure 3:
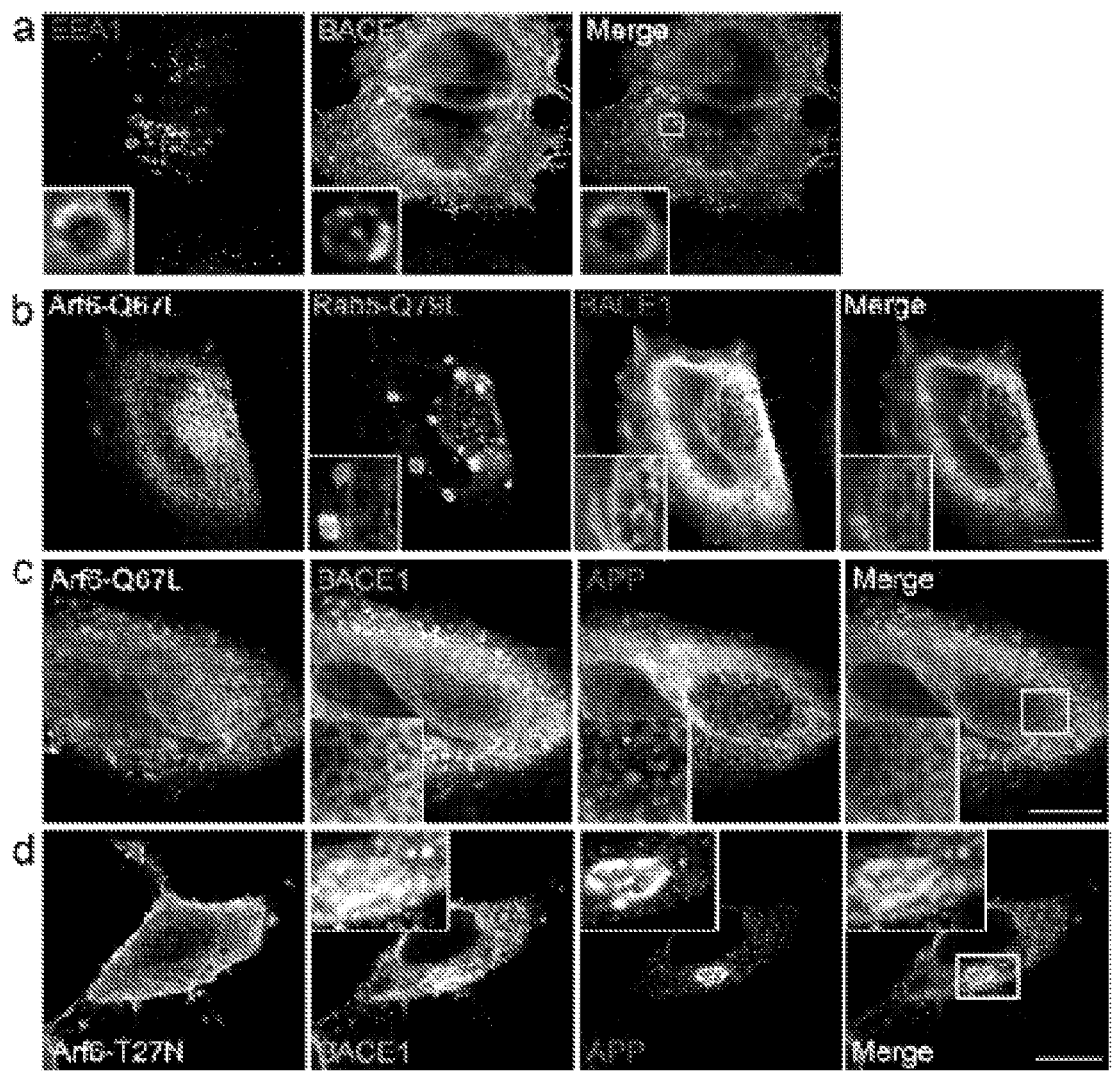
FIG. 3: (a, b) BACE1 internalizes via an ARF6-mediated route before reaching the RAB5 early endosome. (a) HeLa cells were co-transfected with RAB5-Q67L and BACE1, fixed and stained for EEA1 (red) and BACE1 (green). Inset shows a magnification of a selected area indicated by a square in the merge image, to highlight that BACE1 and EEA1 are labeling distinct domain in RAB5-enlarged endosome. Note that BACE1 is present only in a subset of RAB5-enlarged endosomes labeled with EEA1. (b) HeLa cells were co-transfected with cerulean-RAB5-Q79L, HA-tagged ARF6-Q67L and BACE1, fixed after 24 hours and stained using antibodies against HA and BACE1. Pseudo color was used for cerulean-RAB5-Q79L to facilitate visualization and co-localization. RAB5-enlarged endosomes are devoid of BACE1 as shown in the inset picture, which represent only BACE1 (red) and cerulean-RAB5-Q79L (green). (c, d) ARF6-Q67L over-expression prevents BACE1 from reaching APP, while both co-localize in ARF6-T27N compartments. HeLa cells transfected with BACE1 and APP, and with either HA-ARF6-Q67L (a) or HA-ARF6-T27N (b), were fixed and stained for BACE1, APP and HA. Magnification of a selected area is indicated by a square in the merge image. Bar=10 µm.

It has been described that early endosomes, the typical recipient of clathrin-mediated endocytic organelles, constitute a major site of BACE1 activity (Rajendran et al. 2006; Schneider et al. 2008). However, in these studies, BACE1 itself was not yet convincingly shown to reside in early endosomes. By using the dominant active RAB5-Q79L mutant, a GTP-locked RAB5 that blocks exit and maturation from early endosomes causing them to enlarge (Stenmark et al. 1994; Rink et al. 2005), we now clearly show that co-expressed BACE1 readily accumulated in distinct domains of enlarged endosomes (FIG. 3, panel a). This was further confirmed by antibody uptake experiments where internalized antibody-BACE1 conjugates reached RAB5-Q79L-positive endosomes (data not shown). On the other hand, no significant uptake of BACE1 antibodies was detected in cells co-expressing the GDP-bound RAB5-S34N mutant (data not shown). This is interesting since it accords with a proposed role of RAB5 in macropinocytosis. Indeed, such a route from ARF6-dependent internalization to RAB5-positive early endosomes is described for certain ARF6 cargo molecules, such as MHCI and CD59 (Naslaysky et al. 2003; Grant and Donaldson 2009). To investigate whether BACE1 follows a similar route, we co-expressed BACE1 together with both ARF6-Q67L and RAB5-Q79L. In this case, and as opposed to RAB5-Q79L alone, no significant immunolabeling for BACE1 was detected in RAB5-Q79L enlarged endosomes, clearly indicating that BACE1 reaches the RAB5-positive endosomes via the ARF6-mediated route (FIG. 3, panel b). Next, cargo is sorted to endosomal recycling compartments from where proteins like MHCI are recycled to the cell surface again in an ARF6-dependent manner. This formation of recycling tubules can be blocked by over-expressing the GDP-locked ARF6-T27N mutant and when applied here, this indeed resulted in the perinuclear accumulation of BACE1 (FIG. 1, panel b). Even more, in triple-transfected cells, both BACE1 and APP accumulated after ARF6-T27N-mediated blockade of recycling as opposed to the effect of ARF6-Q67L (FIG. 3, panels c and d).

Altogether, the above data imply that BACE1 and APP, enzyme and substrate, respectively, can enter the cell via two distinct routes. BACE1 internalizes majorly via an ARF6- dependent clathrin-independent pathway and that as previously described (Schneider et al. 2008), APP endocytosis is clathrin mediated.

Example 2

Modulation of the Clathrin-Independent ARF6-Mediated Endocytotic Pathway Affects the Processing of APP As shown in Example 1, the ARF6 cycling mutants had an opposite effect on the co-localization of BACE1 and APP, with the ARF6-Q67L clearly blocking BACE1 transport prior to encountering APP. Here, it was investigated how these mutants affected the processing of APP.

Figure 4:
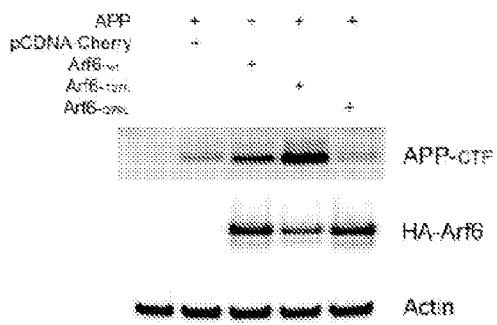
FIG. 4: APP processing is affected by over-expression of the ARF6 mutants. (a) HeLa cells co-transfected with APP and with ARF6-wt, ARF6-Q67L or ARF6-T27N were lysed and total protein (20 µg per lane) were analyzed by Western blot, shown on the left and quantification of APP processing was estimated by dividing APP-CTF fragment to APP full length for each ARF6 construct, right panel. (b, d) Modulating ARF6 cycle activity affects APP processing. (b, c) HeLa cells were transfected with swAPP together with either empty vector or ARF6-WT or ARF6-Q67L or ARF6-T27N or EFA6-WT or EFA6-mut or ACAP1-wt or ACAP1-mut and further process for metabolic labeling experiment 24 hours later as described in materials and methods. Means of ratio Aβ/APP-FL were calculated for each transfection and normalized to the control sample (swAPP with empty vector, ***, $p<0,1\%$). (d) Twenty-four hours after ARF6 down-regulation, cells were transfected with swAPP and 24 hours later, cells were processed for metabolic labeling experiment. ARF6 was ~80% down-regulated after 48 hours (inset). NS=non specific sequence RNAi (*, $p<5\%$).
Figure 4:
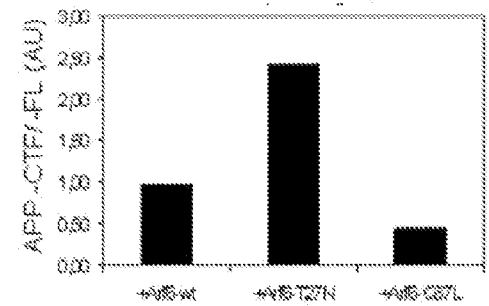
Figure 4:
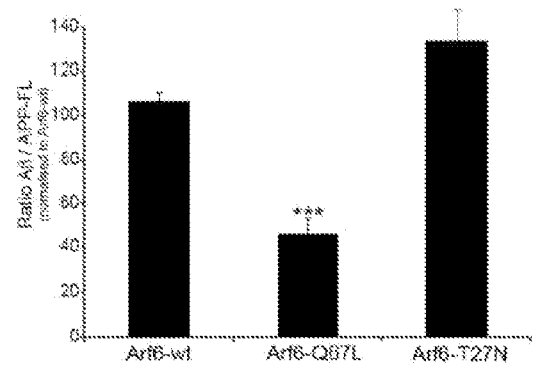
Figure 4:
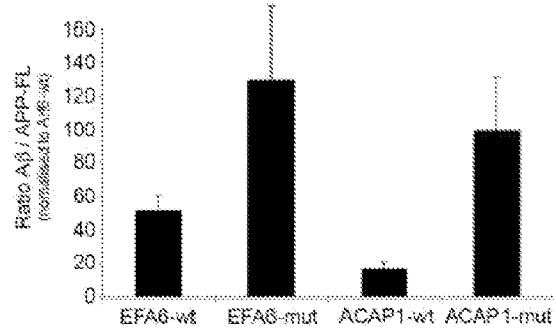
Figure 4:
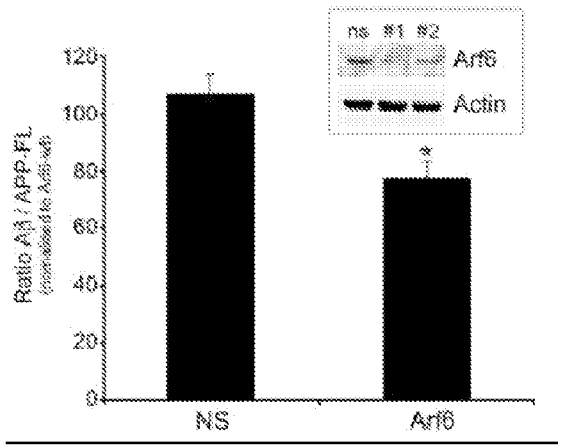

First, we looked at the effect of wild-type and mutants ARF6 on APP processing using quantitative Western blotting. Over-expression of APP with ARF6-Q67L resulted in a nearly 50% drop in the ratio of APP-CTF over full-length APP, while the ARF6-T27N caused a 2.5-fold increase (FIG. 4, panel a). We next moved to metabolic labeling allowing us to evaluate in more detail the effects of wild-type versus mutant ARF6 on newly synthesized Swedish APP (sweAPP). This mutant was chosen as it increases β-secretase processing due to two mutations at codons 670 and 671 ($APP_{770}$ transcript) at the N-terminus of the Aβ sequence (Mullan et al. 1992). Like for APP-CTF, ARF6-Q67L caused a dramatic decrease in both the secretion of soluble ectodomain fragments of sweAPP (APPs as well as Aβ peptides indicating that overall processing of sweAPP was strongly inhibited in ARF6-Q67L-expressing cells (FIG. 4, panel b). On the other hand, ARF6-T27N expression had an adverse effect on sweAPP processing, resulting in more secreted APPs and Aβ as compared to wild-type ARF6 over-expression (FIG. 4, panel b). However, it was surprising to find that these increases were statistically not significant. This could be explained by the assumption that despite the increased shedding, the ARF6-T27N-mediated transport blockade also affected the accessibility of APP-CTFs to become processed by γ-secretase. This is at least supported by the stronger accumulation of APP-CTF in these cells (FIG. 4, panel a), although alternative explanations cannot be excluded. To further scrutinize the importance of ARF6 activity on BACE1 trafficking and, hence, APP processing, we explored the effect of (hyper) activating the ARF6 cycle by over-expressing the ARF6 specific GEF, EFA6a (Franco et al. 1999) and GAP, ACAP1 (Jackson et al. 2000), that promote the GTP- and GDP-bound state of ARF6, respectively. In both cases, over-expression resulted in a significant decrease in secreted APPs (not shown) and Aβ FIG. 4, panel c). On the other hand, over-expressing their respective mutant EFA6A and ACAP1 did not affect Aβ secretion as compared to mock transfection. This suggested that the observed effects are caused by the respective increased GEF and GAP activity on ARF6 function, possibly resulting both in a preference towards the GTP-bound state of ARF6. It is not surprising, therefore, that both effectors have a similar effect on APP processing as observed for ARF6-Q67L. Finally, we investigated the effect on APP processing when the ARF6 route overall was suppressed. As shown in FIG. 3, Panel d inset, siRNA-mediated down-regulation of endogenous ARF6 resulted in nearly 80% reduced protein levels as compared to non-specific oligonucleotides. This significantly reduced Aβ secretion, albeit not to the extent as observed by a more dramatic blockade of ARF6-mediated transport, for instance, using ARF6-Q67L.

Figure 5:
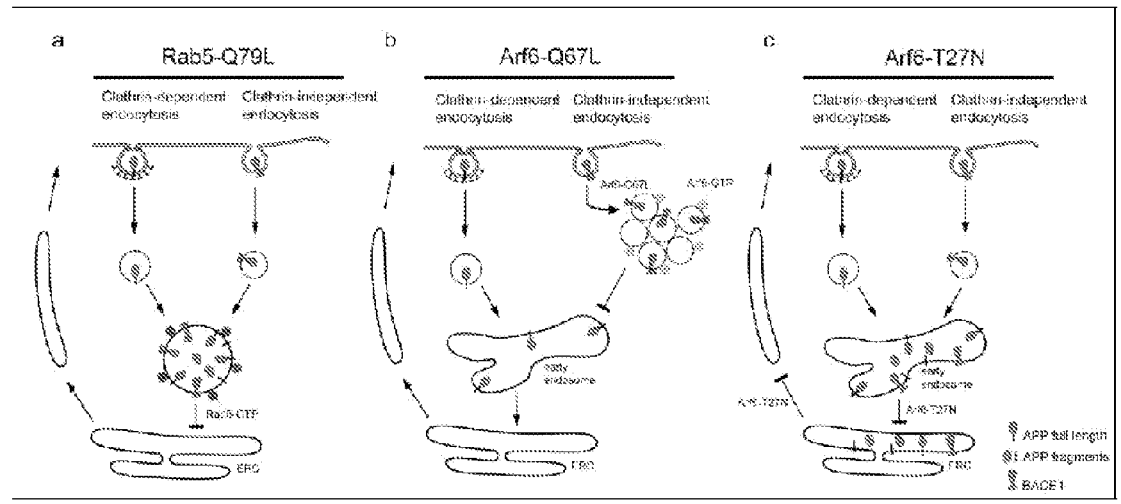
FIG. 5: Differential sorting of BACE1 and APP. Schematic representation of BACE1 and APP trafficking within the endosomal system in cells over-expressing RAB5-Q79L (a), ARF6-Q67L (b) and ARF6-T27N (c). (a) Cells over-expressing RAB5-Q79L develop enlarged endosomes where APP and BACE1 accumulate promoting processing. (b) Over-expression of ARF6-Q67L blocks the fusion of ARF6 vesicles to endosome ending up with a massive accumulation of vacuoles, which trap BACE1 preventing its trafficking to the endosomes and therefore cleavage of APP. (c) Blocking ARF6-dependent recycling promote APP processing.

Altogether our data demonstrate that BACE1 and APP enter the cell/neuron via two distinct routes, a clathrin-independent/ARF6-dependent and clathrin-dependent one, respectively (FIG. 5). Over-expression of ARF6-Q67L blocks the transport of BACE1 at an early stage, preventing it from reaching the early endosome and, hence, access to its major substrate APP (FIG. 5, panel b). The net result is a prominent decrease in proteolysis. On the other hand, inhibiting BACE1 recycling to the cell surface using ARF6-T27N, enhances residence time of both BACE1 and APP, resulting in increased processing (FIG. 5, panel c). Hence, keeping BACE1 and APP separated until they encounter each other in the early endosome provides a clear physiological means to control ectodomain shedding and, hence, Aβ production.

In addition, our data suggest that BACE1 utilizes this selective ARF6 route for balancing its levels in the cell and neuron. Indeed, the ARF6-mediated endocytosis as a degradative route has also been previously described for the epidermal growth factor (EGF) receptor (Sigismund et al. 2008). When cells are treated with high (200 ng/ml) EGF doses, a pool of the EGF-receptor becomes internalized via an ARF6-dependent route for degradation instead of the clathrin-mediated pathway, which promotes recycling (Sigismund et al. 2008). Similarly, high EGF concentrations, a condition that stimulates macropinocytosis, also enhances BACE1 internalization (this study; Lanzetti et al. 2004; Zou et al. 2007; Frittoli et al. 2008), which, by this mechanism, allow the cell to adapt and regulate the amount of protein at the cell surface. Our data also provide a cell biological explanation for the inverse correlation of BACE1 and GGA3 expression levels described earlier (Tesco et al. 2007). Indeed, down-regulation of GGA3 was shown to inhibit macropinocytosis (Frittoli et al. 2008) and, hence, decreased levels of GGA3 as, for instance, observed in AD brain, prevents BACE1 from being sorted in the ARF6-dependent pathway and instead stabilized.

Although the major site of Aβ generation has been assigned to endosomal compartments, we now prove for the first time that BACE1 reaches this compartment independently from APP via a clathrin-independent/ARF6-mediated route. Our study, therefore, not only increases significantly our understanding of the intracellular transport regulation of BACE1 versus APP, but, moreover, demonstrate that sorting of BACE1 and APP can be independently obstructed by interfering with their respective endocytic machineries, as shown with ARF6 mutants but also with AP180-C. This implies that factors or compounds selectively affecting internalization of BACE1 or APP, may provide a yet unexplored avenue for therapeutic inhibition of Aβ production in AD.

Example 3

Figure 6:
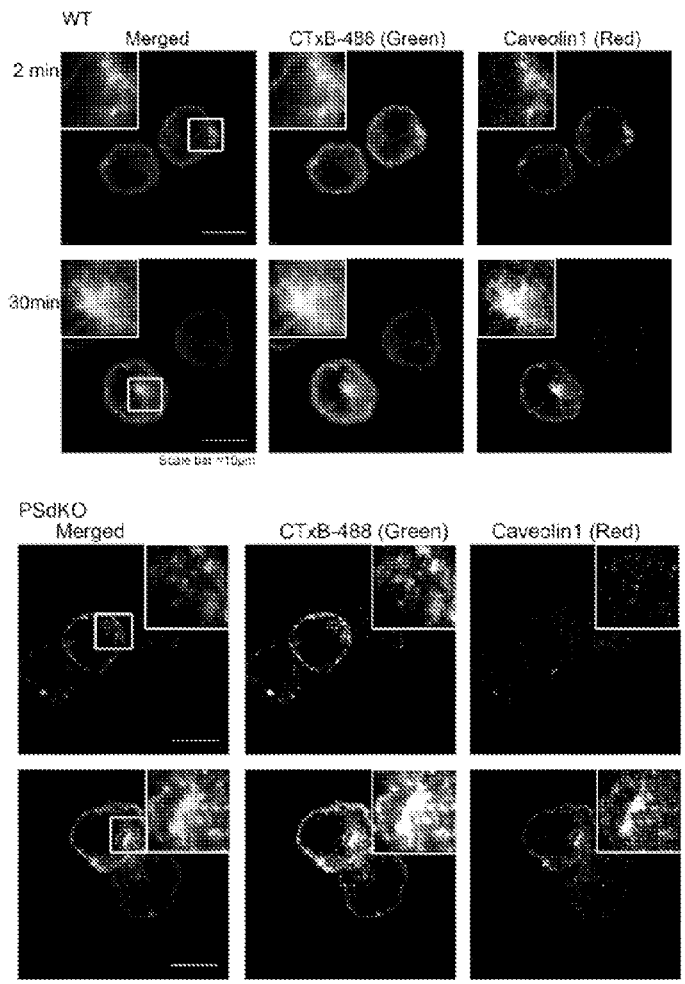
FIG. 6: Adhesion-dependent raft endocytosis towards the perinuclear recycling compartment is not affected by presenilin deficiency. Stably adherent fibroblasts were plasma membrane-labeled with CTxB-AlexaFluor488 on ice, and brought in suspension for the indicated times. Cells were kept at 37° C. during the suspension phase and, after fixation, immunofluorescently labeled for caveolin1. The central region is enlarged in the left panel. In both, WT and PSEN1&2dKO MEFs raft markers are localized in the perinuclear region of the cell after 30 minutes in suspension.
Figure 7:
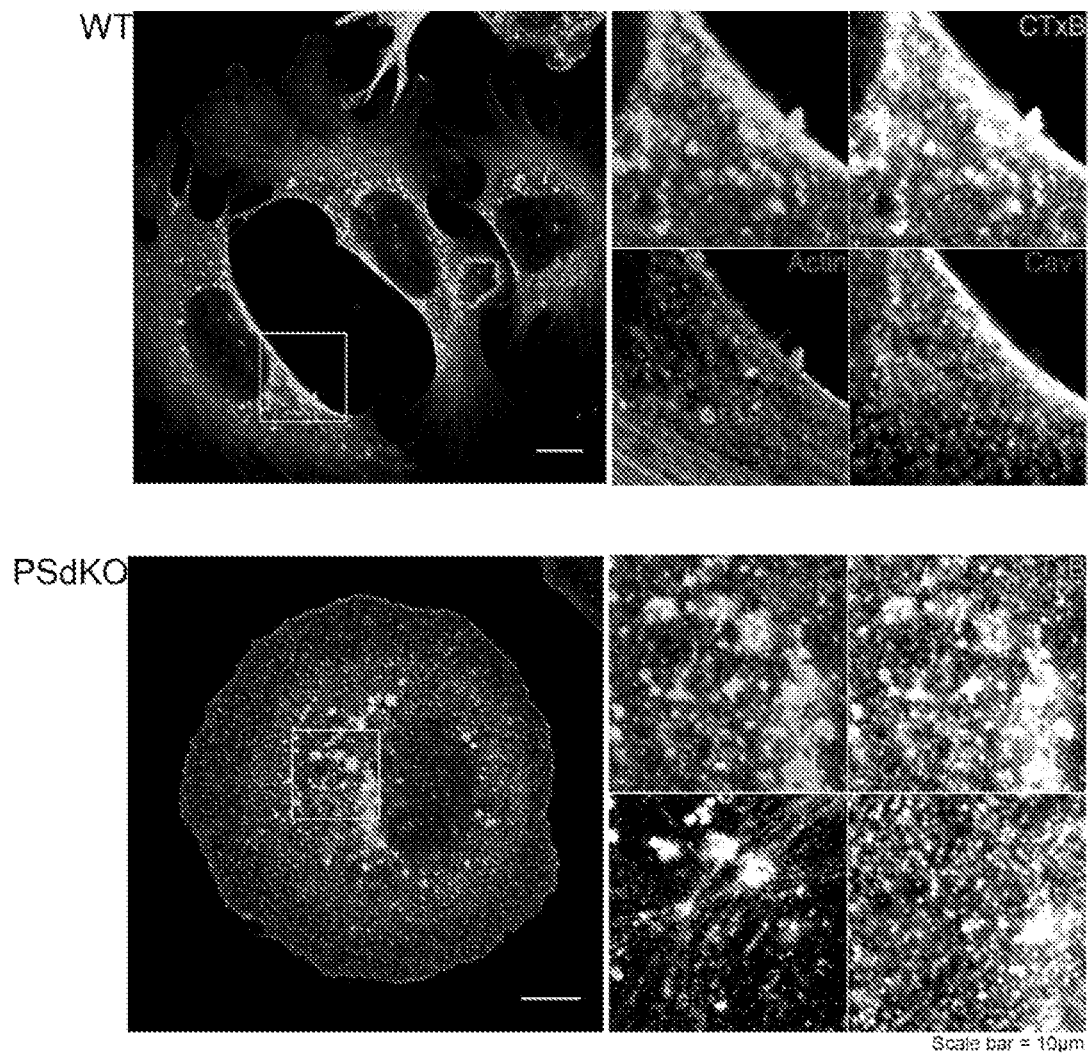
FIG. 7: Redistribution of raft components from the recycling compartment are blocked in PSEN1&2dKO MEFs. After one hour in suspension, fibroblasts were replated on a fibronectin-coated surface (20 µg/ml) for one hour. In WT MEFs, the raft markers CTxB and caveolin1 redistribute back to the plasma membrane in a polarized manner, while in PSEN1&2dKO cells, both remained largely in the perinuclear region. Caveolin1 distribution is much more fragmented in fine spots compared to WT cells and does not reach the plasma membrane at all.
Figure 8A:
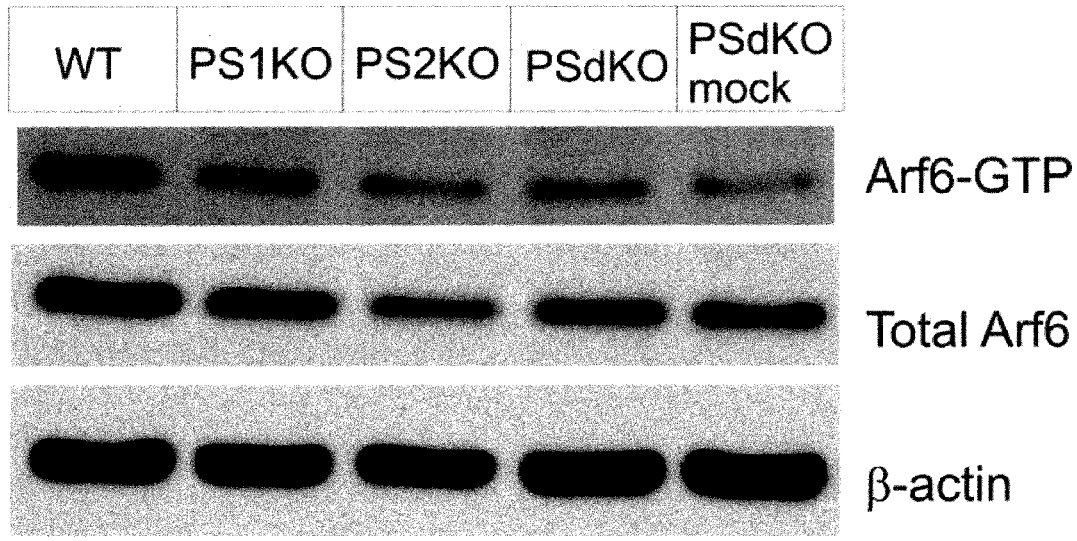
FIG. 8: ARF6 activity is deregulated at the mRNA level in presenilin deficient fibroblasts. (a) WT and PSENKO MEFs were lysed, and active ARF6 was pulled down on GST-GGA3 beads. Representative Western blots of bound samples (ARF6-GTP) and the respective whole cell lysates (total ARF6) show a clear decrease in ARF6 activity in all PSKO cell lines. Blots from at least three independent experiments were quantified, and normalized intensities were calculated relative to WT MEFs for total ARF6 (b), and the ratio of ARF6-GTP to total ARF6 (c). (d) RTqPCR results indicate that the reduction in ARF6 activity was partially caused by a decrease in mRNA levels in PSENKO cells. (N=3-7; means±SEM; * $P<0.05$,  $P<0.01$, * $P<0.005$).
Figure 8B:
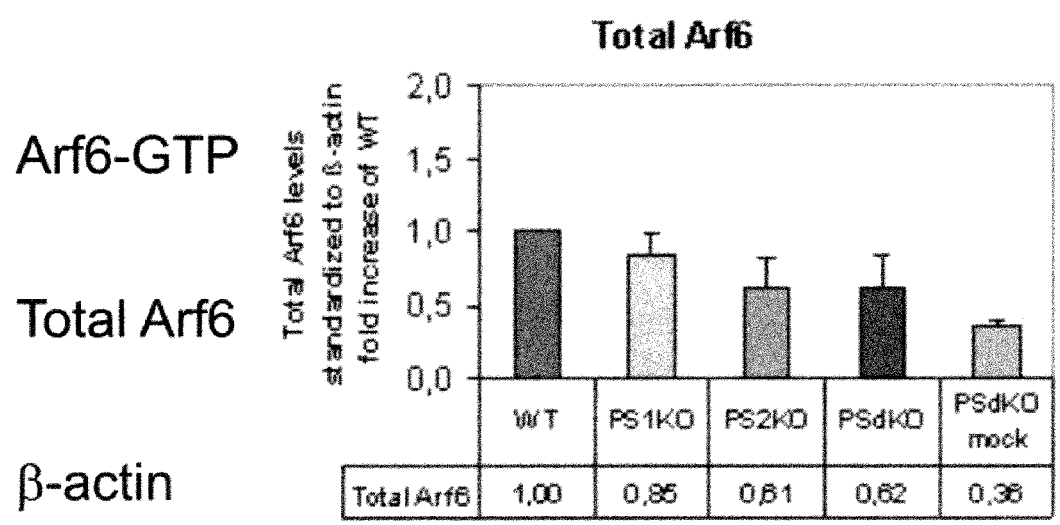
Figure 8C:
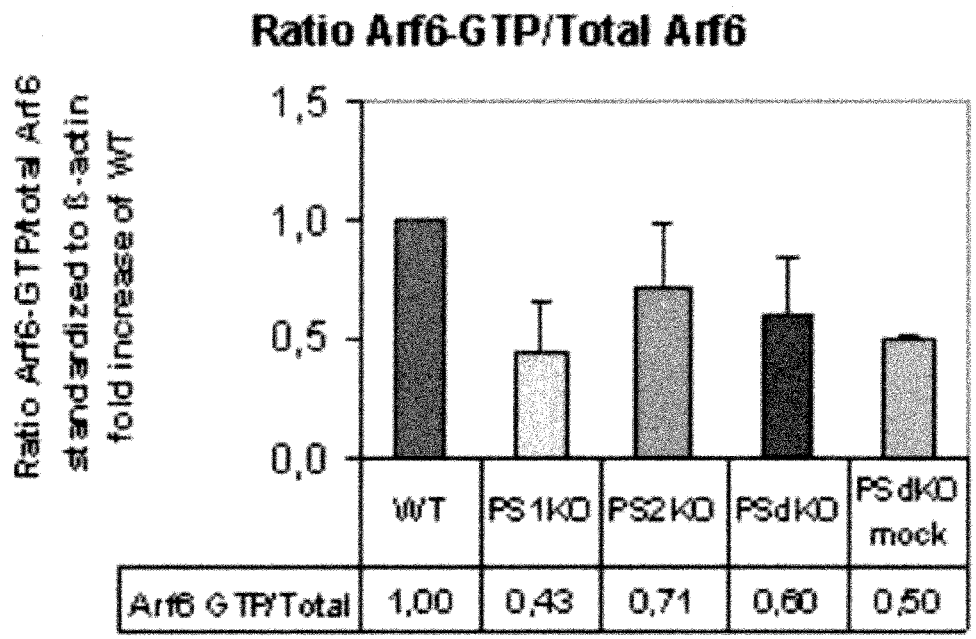
Figure 8D:
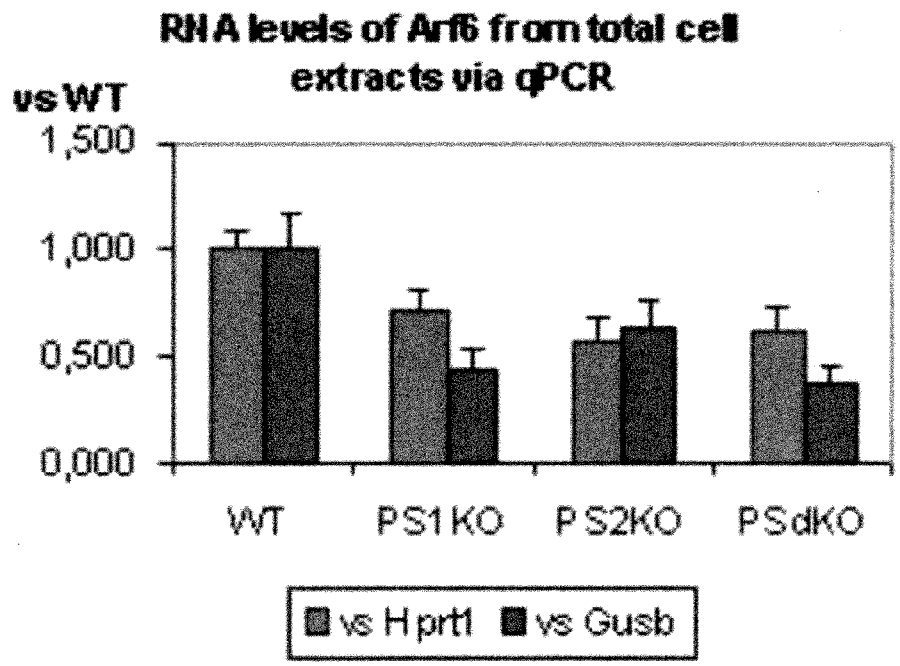
Figure 9:
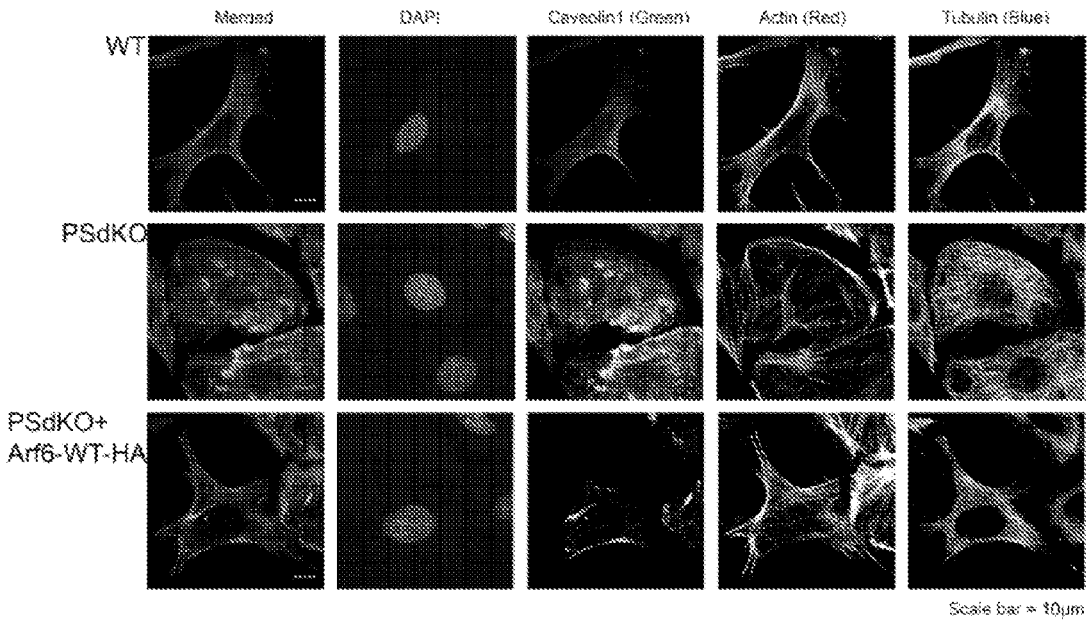
FIG. 9: Confocal microscopy of MEF cells immunolabeled for endogenous caveolin1 (Green), β-actin (Red), and α-tubulin (Blue) reveals in more detail the aberrant morphology of PSEN1&2dKO MEFs. In WT cells, caveolin1 shows a polarized plasma membrane localization at one edge of the cells. However, immunoreactivity of caveolin1 in PSEN1&2dKOs is clustered intracellular, with only very little plasma membrane staining left. PSEN1&2dKO revert to WT morphologies upon retroviral transduction with hARF6-WT, including a polarized redistribution of caveolin1 to the plasma membrane.

Retroviral Expression of Human ARF6 in a PSEN Double Knockout Cell Line and its Use in Screening Assays Presenilins (PSEN1 and 2) can act in a γ-secretase-independent manner regulating cell migration and endocytosis. The migration and adhesion defects of PSENKO cells are likely caused by problems in caveolin1 transport and redistribution from intracellular caveosomes. Therefore, the role of PSENs in adhesion-dependent endocytosis and recycling pathways of raft proteins in wild-type (WT) versus PSEN1 and 2 dKO MEFs was tested. Adherent fibroblasts were pre-labeled with CTxB, specifically labeling the raft marker GM1. CTxB and caveolin1 localize sharply at the plasma membrane immediately after detachment, and accumulate in the perinuclear region after 30 minutes in suspension. Despite significant differences in the steady state localization of caveolin1 in PSENKO MEFs (FIG. 9), there was no delay in the uptake kinetics toward the intracellular recycling compartments during the suspension phase (FIG. 6). After one hour in suspension, fibroblasts were re-plated on a fibronectin-coated surface for one hour. In WT MEFs, this resulted in the polarized redistribution of caveolin1 and CTxB to the plasma membrane. In PSEN1 and 2 dKO cells, the dynamic re-localization of CTxB and caveolin1 was not apparent, and both molecules remained largely in the perinuclear region. Caveolin1 distribution is much more fragmented in fine spots in PSEN1 and 2 dKO cells, compared to controls and does not reach the plasma membrane at all (FIG. 7).

ARF6 controls the adhesion-regulated recycling of rafts from the recycling endosomes to the plasma membrane (Balasubramanian et al. 2007). Looking at the ARF6 levels in PSENKO MEFs, it was found that total ARF6 levels as well as ARF6-GTP levels were decreased in all PSENKO cells. Via RTqPCR, it was shown that presenilins regulate the amount of ARF6 mainly at the level of mRNA synthesis (FIG. 8). Thus, ARF6 activation, regulated upstream by PSENs, is coupled to the efflux of recycling endosomes and redistribution of raft components. In addition, it was found that retroviral expression of human ARF6 in PSEN1 and 2 dKO cells can rescue the intracellular accumulations of caveolin1, resulting in its polarized plasma membrane distribution at one edge of the cell (FIG. 9) and generating PSENDKO MEFs lacking γ-secretase activity but with a morphology and balanced endosomal trafficking reminiscent of wild-type cells.

Since the internalization and redistribution of GM1-containing membrane domains regulate Rac1 signaling, we speculated that Rac1 does not get internalized upon adhesion, resulting in problems in cell spreading, polarity, and cell migration, as shown for caveolin1 KO MEFs (del Pozo et al. 2004; Grande-Garcia et al. 2007). It is, therefore, not surprising that the normalized caveolin1 distribution in PSEN1 and 2 dKO MEFs expressing human ARF6 results in decreased Rac1 levels (FIG. 10) and a normal fibroblast-like phenotype. These "rescue" cell lines underwent dramatic morphological changes from a round morphology to an elongated cell shape, with reduced lamellipodia formation compared to presenilin-deficient cells. ARF6 expression in PSEN1 and 2 dKO MEFs also compensates for the increased cell migration speed in wound healing assays (FIG. 11).

Figure 10:
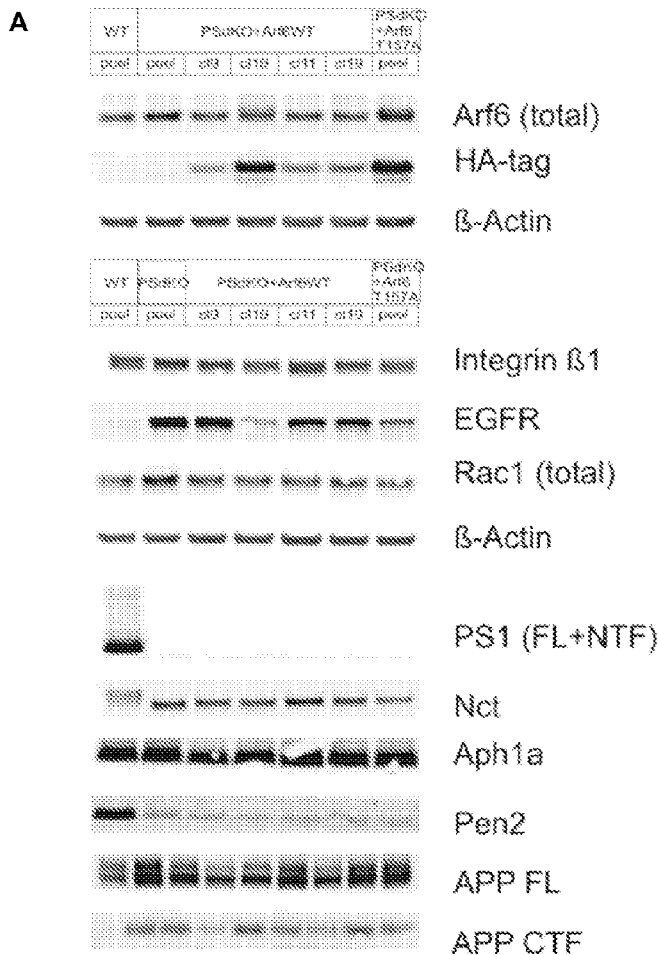
FIG. 10: Expression of human ARF6 "rescues" increased Rac1 and EGFR levels in PSEN1&2dKO MEFs. (A) Western blot analysis of PSEN1&2dKO MEFs retrovirally infected with hARF6 WT-HA or hARf6 T157A-HA shows that Rac1 and EGFR levels decrease dependence on the amount of ARF6 expression (quantified in B). No differences were seen for the stability of the different γ-secretase components, or for APP processing. Therefore, we can postulate that the increase in Rac1 levels and EGFR levels in PSEN1&2dKO MEFs is independent of γ-secretase activity.
Figure 10A:
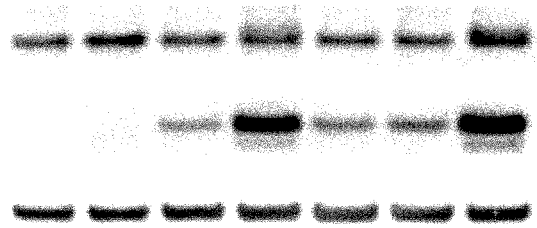
Figure 10A:
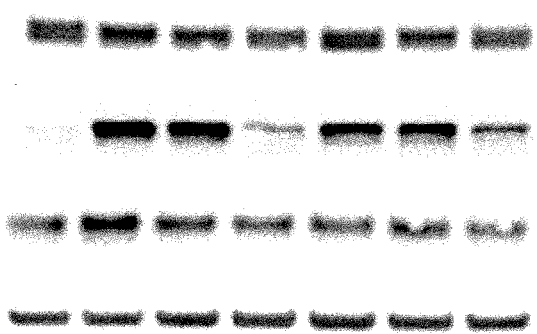
Figure 10A:
Figure 10A:
Figure 10A:
Figure 10A:
Figure 10A:
Figure 10A:
Figure 10B:
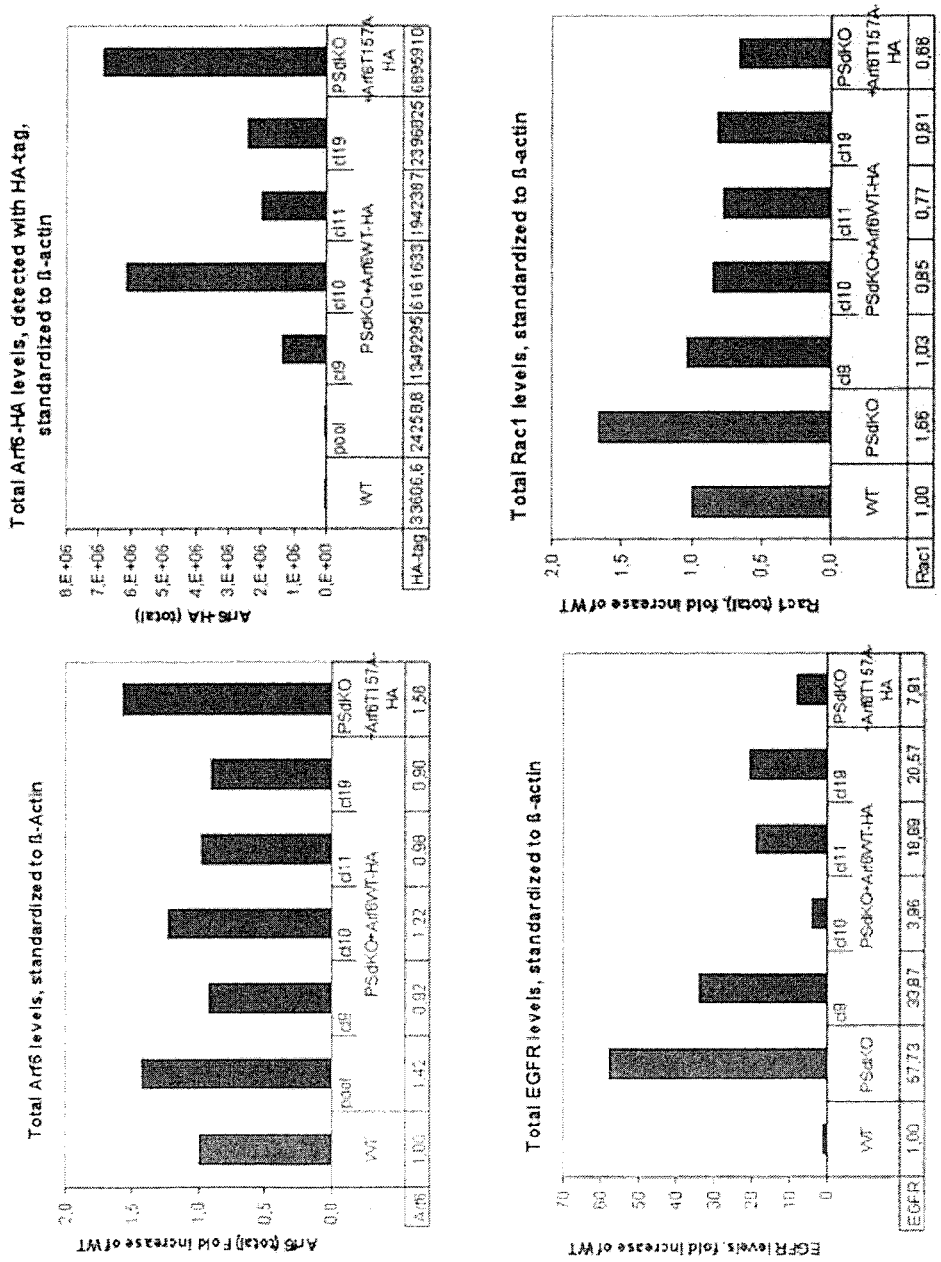

Earlier reports showed that PSEN1 is involved in degradative organelle turnover. Deficiency of PSEN1 in hippocampal neurons leads to the accumulation of ICAM5 (Esselens et al. 2004), and α- and β-synuclein in autophagic vacuoles (Wilson et al. 2004). Similarly to the neuron data, a dramatic increase in the amount of acidified compartments was seen in PSEN1 and 2 dKO MEFs, concomitant with increased anti-EGFR staining compared to control cells (FIG. 12). Retroviral expression of human ARF6 WT in these cells resulted in a dramatic decrease of EGFR expression levels dependent on the amount of ARF6 rescue (FIG. 10). ARF6 is involved in the regulation of protein degradation, resulting in largely diminished acidic accumulations in PSEN1 and 2 dKO cells. Anti-EGFR staining is dispersed over the complete cell due to increased ARF6 expression levels.

Altogether, by "rescuing" the PSENdKO cell line with the ARF6 GTPase, the aberrant morphological phenotype observed in the PSENdKO cell line could be restored. Therefore, the "rescue" cell line allows discrimination between the γ-secretase-independent versus γ-secretase-dependent (catalytic) function and, as such, is a valuable screening tool for new drug compounds.

Example 4

Screening Assay

A morphological screening assay has been set up making use of wild-type (WT) and Presenilin1 and 2 (PSEN1 and 2) knockout Mouse Embryonic Fibroblasts (MEFs). PSEN1 and 2 knockout cells stably rescued with ARF6 are used as a positive control. The screening assay can be dissected in different steps. First cells are brought into culture and several cell lines are maintained. These cells are treated with compounds, incubated and afterward, fixed and stained. These stained cells are imaged and the images are further analyzed. The screening assay was optimized and is described into further detail in the Materials and Methods to the Examples section.

A medium to high throughput screen was performed using a chemical compound library. The chemical genetic screen took advantage of a library of 10,000 compounds available at the Plant Systems Biology department of VIB (Ghent, Belgium).

As an initial screen for morphology, in each well, 50 to 100 cells were randomly analyzed with respect to the surface area they occupy as well as the perimeter. The ratio of surface area to perimeter, defined as "circularity" was read-out to quantify changes in morphology, i.e., changes from more circular, adhesive cells to elongated migratory cells. An example and proof-of-principle is given (FIG. 13) in which the circularity is measured between WT, PSEN1 and 2 knockout and PSEN1 and 2 knockout cells stably rescued with ARF6 as a positive control.

After optimization, five parameters are calculated to study changes in the cell morphology, namely, the cell intensity, cell count, cell roundness, cell area and cell elongation. The ratio of the short over the long axis of the cells is called the cell elongation. A not elongated or symmetric cell has a value of one. All the other values situate between zero and one. The cell roundness is also called the cell 1/form factor. It is calculated via parameter (perimeter) over area. These values lie between one and +infinity. A cell with a roundness of one, forms a perfect circle.

Using this morphology assay we screened about 2,500 chemical compounds out of the available 10,000 compound library (hence 25%). Each compound was analyzed simultaneously in three MEF lines, namely wild-type, PSEN-dKO and PSEN-dKO stably rescued with ARF6, using the InCell 2000 analyzer (GE Healthcare). At the end of the experiment, the morphology of the cells (i.e., along the parameter of "roundness") was evaluated and scored. From the 2,500 chemical compounds, we could identify 23 positive hits. With "positive hits" we mean those compounds that affect the morphological parameter of PSEN-dKO MEFs but not that of wild-type and ARF6-rescued MEFs. Such compounds likely affect the morphology of PSEN-dKO MEFs through acting on up- or downstream effectors of the ARF6 pathway or signaling.

Positive hits are further analyzed on the basis of the following parameters:
 Localization of endogenous caveolin 1 in these MEF cell lines
 Accumulation (and its rescue) of lysotracker in acidic endosomal compartments
 Uptake of fluorescently tagged Epidermal Growth Factor (EGF)
 Measurement of APP processing after metabolic labeling

Example 5

Endogenous ARF6 Levels Decrease with Aging

Given the findings in Example 2 that interfering with ARF6 activity affects APP processing and, in Example 3, that ARF6 levels are down-regulated in PSEN-deficient cells, it follows that we hypothesized that endogenous ARF6 expression levels may undergo changes during aging of the brain. We analyzed extracts of brain cortices obtained from mice at different stages of development (prenatal and early postnatal days and weeks) up to adult mice, between 6 months and 24 months of age, the latter referred to as old or aged mice. Using quantitative Western blotting of endogenous ARF6 protein expression levels, normalized to endogenous GAPDH protein expression levels, we observe an increase of ARF6 protein expression during late embryonic development and postnatally. However, these levels dropped from 3 months onward to over 50% between 6 and 24 months (FIG. 14). In contrast, endogenous RAB5, a major RAB GTPase involved in early endosomal sorting, remains, after an increase during embryonic stages, very stable up to 24 months, underscoring a selective vulnerability for ARF6 and the ARF6 pathway. Interestingly, also endogenous presenilin1 protein levels decrease to a similar extent from 1 month onward to 24 months. This agrees well with the observed lower ARF6 levels in presenilin1-deficient cells and neurons and highlights a genetic interaction between both.

Example 6

ARF6 Levels are Down-Regulated in the Brain of Alzheimer's Disease Patients

As ARF6 levels decrease during aging in mice, we challenged the idea that a similar event occurs in brains for Alzheimer's disease (AD) patients. To investigate this, we obtained brain samples of the frontal cortex of human control and AD brain (Brainbank of Lille, in collaboration with Prof. Em. A Delacourte). Protein extracts were analyzed by quantitative Western blotting and normalized to endogenous GAPDH. As a control, we compared the levels of endogenous RAB5 (see Example 5) as well as the adaptor molecule GGA3. The latter has been demonstrated to be down-regulated in AD brain and is an interactor of BACE1 (Tesco et al. 2007). We observe that both ARF6 and GGA3 are down-regulated in AD brain, as compared to control brain samples. Again, endogenous RAB5 levels are not altered, not only underscoring the reliability of quantitative Western blotting but also the selectivity in affected endosomal regulators. Of importance is also the recent observation that GGA3 interacts with TBC1D3 and that over-expression of TBC1D3 activates the ARF6-mediated macropinocytotic route. It is, therefore, not surprising that both ARF6 and GGA3 levels are lowered as they operate in the same internalization/endosomal route.

Materials and Methods to the Examples
Cell Culture

HeLa (CCL2 clone) cells were routinely grown in Dulbecco's modified Eagle's medium (DMEM/F12, Invitrogen) supplemented with 10% fetal calf serum and maintained in a humidified chamber with 5% $CO_2$ at 37° C. The culture of primary hippocampal neurons has been described previously [1].

Antibodies

The following monoclonal antibodies (mabs) were commercially obtained: Rat mab against theHA tag (clone 3F10, Roche Diagnostics), mab to ARF6 (SC-7971, Santa Cruz); mab to MHCI (clone W6/32, Abcam), mab to CD59 (Chemicon); mab to FLAG (clone M2, Sigma), and mab to GGA3 (clone 8, BD transduction Laboratories); mab to transferrin receptor (TFR, clone H68.4, Invitrogen) and mabs to Aβ (6E10, 4G8, Signet Laboratories). Rabbit polyclonal antibodies (pabs) were obtained from: anti-APP (A8717, Sigma); and anti-myc (clone A-14, Santa Cruz). Pab to APP (B63) has been described previously (Esselens et al., JCB 2004) and generated using a synthetic peptide corresponding to the final 16 amino acids of APP coupled to KLH (Pierce Chemical Co.) as an antigen.

A monoclonal antibody ("mab"), 10B8, against BACE1, was produced in house by immunizing BACE1−/− mice with recombinant hBACE1 ectodomain followed by generation of a hybridoma cell line according to established procedures (Esselens et al. 2004).

Plasmids, Transfection, RNAi

Plasmids encoding ARF6 proteins (pXS-HA-ARF6wt, pXS-HA-ARF6Q67L and pXS-HA-ARF6T26N) were generously provided by J. Donaldon (NIH, Bethesda, Md., USA); myc-tagged Aβ 180C was from H. McMahon (MRC, Cambridge, UK), GFP-EFA6 from P. Chavrier (Institut Curie, Paris, France), HA-tagged TBC1D3 and FLAG-tagged GGA3 were from S. Confalonieri (IFOM, Milan, Italy); Rab5Q79L from M. Zerial (MPI, Dresden, Germany), ACAP1-wt and ACAP1-R448Q from V. Hsu (Harvard Medical School, Boston, USA) and finally pcDNA-hBACE1 from C. Haass (Ludwig-Maximilians-Universität Adolf-Butenandt-Institute, Germany).

cDNAs of wild-type APP695 and the Swedish mutant, APPsw, were cloned into pcDNA-3.1 (Zeo+) vector (Invitrogen). ARF6 constructs were recloned into pcDNA as follows: HA-tagged ARF6T27N using EcoRI and XbaI, and ARF6Q67L using EcoRI and EcoRV restriction sites. All cDNAs were verified by sequencing.

HeLa cells were transfected with FugeneHD (Roche Diagnostics) and primary neurones with Lipofectamine 2000 (Invitrogen) as described by the manufacturers.

The siRNA sequence targeting ARF6 are oligo#1: 5'-GCACCGCATTATCAATGACCG-3' (SEQ ID NO:1) and oligo#2: 5'-GGTCTCATCTTCGTAGTGG-3' (SEQ ID NO:2) [2]. Oligo#1 was used for metabolic labeling experiments. The GL2 luciferase RNAi duplex was used as a non-specific control. RNAi duplexes were manufactured by Dharmacon, Lafayette, Colo. and transfection was done using Oligofectamine (Invitrogen) as described by the manufacturer. Cells were analyzed 48 hours after down-regulation.

Confocal Laser Scanning Microscopy

Cells were routinely plated on glass cover slips, transfected 24 hours later and processed for indirect immunolabeling the next day. After fixation (4% paraformaldehyde/4% sucrose in PBS, 20 minutes RT) and washing, cells are permeabilized (0.1% Triton in PBS, 5 minutes RT) and blocked (2% bovine serum albumin (BSA), 2% fetal bovine serum (FBS), 1% gelatin, 2% goat serum in PBS, 1 hour, RT). Primary antibodies were diluted in the same blocking buffer and applied to fixed cells (4° C., overnight). Following washes in PBS, cells were incubated with the appropriate secondary antibodies conjugated to either Alexa-488, -568, -647 or Pacific Blue (Invitrogen) diluted in blocking buffer (1 hour, RT). Finally, cells were washed and mounted with Mowiol. Images were captured on a confocal microscope (Radiance 2100; Carl Zeiss MicroImaging, Inc.) connected to an upright microscope (Eclipse E800; Nikon) and using an oil-immersion plan Apo 60×A/1.40 NA objective lens. Image acquisition and final processing was done with Lasersharp (v . . . , Zeiss) and Adobe Photoshop 8.0 (Adobe, Calif.).

Primary Antibody Uptake hBACE1- or APPwt-transfected cells were serum-starved for 4 hours, rinsed twice with ice-cold serum-free medium and incubated with the appropriate primary antibodies (mab 10B8 for BACE1 and 6E10 for APP) diluted in serum-free medium on ice for 30 minutes. Then, cells were rinsed twice with ice-cold serum-free medium to remove unbound antibodies and placed back in the incubator at 37° C. for 10 minutes in pre-warmed medium containing 200 ng/ml EGF (Sigma), to stimulate macropinocytosis [3] or kept on ice for the controls. Internalization was stopped by putting cells on ice, and replacing the medium with washes with ice-cold PBS. Following fixation (4° C., 20 minutes), but prior to permeabilization, remaining cell surface-bound antibodies were first immunolabeled by incubating cells with Pacific-Blue-conjugated secondary antibodies (1 hour). Then cells were rinsed and permeabilized (0.1% Triton X-100 in PBS, 5 minutes) and blocked (see above). Internalized primary antibodies were immunolabeled by incubating cells with appropriate Alexa-tagged secondary antibodies. Imaging and processing was done as described above.

Cell Surface Biotinylation and Internalization Assay

All reagents, except otherwise stated, were kept on ice. Following 24 hours transfection with the appropriate constructs, HeLa cells were placed on ice, washed in PBS (pH 8) and next incubated in PBS (pH 8) supplemented with 0.25 mg/ml sulfo-NHS-SS-Biotin (Pierce) (15 minutes at 4° C.). Excess of biotin was washed out, and cells were incubated with 1% BSA in PBS (10 minutes at 4° C.). After removing BSA, cells were incubated at 37° C. for the appropriate time or kept at 4° C. as a control. Endocytosis was quickly stopped by placing the dishes back on ice and washing the cells with ice-cold PBS. Remaining biotin at the cell surface was cleaved off by incubating the cells twice in PBS containing 100 mM 2-sodium-2-mercaptoethanesulfonate (Sigma) as a reducing agent (15 minutes at 4° C.). To determine total surface biotinylation, cells were incubated in PBS lacking the reducing agent. After this, cells were washed with ice-cold 5 mg/ml iodoacetamide for 5 minutes, then twice with ice-cold PBS, and finally extracted in lysis buffer (50 mM HEPES, pH 7.2, 100 mM NaCl, 1% Triton X-100, +proteases inhibitor cocktail (Sigma)). Total protein was measured and biotinylated proteins were pulled down from equal amounts of extracts using streptavidin Sepharose beads (Pierce) (4° C., overnight on a rotation wheel). After washing, the bound material was eluted from the beads using 2× loading buffer (Invitrogen) containing 2% β-mercaptoethanol (70° C. for 10 minutes), separated on pre-casted 4-12% Bis-Tris NuPAGE gels in MES running buffer (Invitrogen) and processed for Western blotting and immunodetection. For each data point, three samples were prepared, one being non-reduced (NR) but kept at 4° C. during the whole procedure (hence representing the total pool of surface biotinylated proteins), one reduced (R0) but kept at 4° C. (to monitor the efficiency of reduction of biotin) and finally one reduced (R37) following internalization at 37° C. (representing the internalized pool of proteins). To compare the internalization efficiency for each protein, the (R37-R0)/NR ratio for each experiment was measured and normalized to the control (contro=100). Each experiment was performed at least three times and statistical significance was measured using two-sided Student t-test. Values are presented as mean±SEM.

Protein Determination and Western Blotting

Protein concentrations were determined by the Bio-Rad DC protein assay (Bio-Rad) as described by the manufacturers. Samples were separated by SDS-PAGE (4-12% Bis-Tris NuPAGE gels in MES running buffer (Invitrogen) and transferred onto nitrocellulose membranes (Invitrogen). After blocking in 5% non-fat milk, membranes were incubated with primary antibody (4° C., overnight) followed by washing and incubation with horseradish peroxidase (HRP)-conjugated secondary antibodies (1 hour, RT). After final washing, immunodetection was done using a chemiluminescence reaction (Western Lightning-Plus ECL reagent (PerkinElmer)), and immunoreactive protein bands were digitally processed and quantified on a Fuji MiniLAS 3000 imager (Fuji) and using Aida software raytest (Isotopenmessgeräte GmbH, Germany).

Metabolic Labelling

Twenty-four hours after transfecting HeLa cells with pcDNA-APPsw, cells were washed twice with serum-free and once with methionine- and cysteine-free medium (Sigma) supplemented with 2 mM L-glutamine, 0.5 mM sodium pyruvate, and Pen/Strep (100 units/ml) (Invitrogen) and incubated (10 minutes at 37° C.). Medium was replaced with the same fresh methionine- and cysteine-free medium (Sigma) but additionally supplemented with 0.07 mCi $[S^{35}]$ translabel (EasyTag Express Protein labeling Mix, Perkin Elmer). After 3 hours at 37° C., the conditioned medium was collected and the cell layer was washed once in PBS, and then scraped in extraction buffer (1× Tris-buffered saline (TBS: 50 mM Tris.HCl (pH 7.4) and 150 mM NaCl), 1% Triton X-100, Complete protease inhibitor cocktail (Roche Diagnostics)). Both the conditioned media and cell extracts were centrifuged (14,000 rpm, 20 minutes) to remove detached cells and unsolubilized material). Cleared conditioned media were first immunoprecipitated with mab 4G8, then the unbound fraction was split in two and used to immunoisolate secreted APPβ ectodomain and Aβ peptides using pab ANJJ (4 µl) [4] and 6E10 (3 µl), respectively, together with protein G-Sepharose (Pharmacia) (overnight, at 4° C., on a rotating wheel). Full-length APP and APP-CTFs were isolated likewise from extracts using pab B63. Immunoprecipitates were washed five times in extraction buffer, once in TBS and bound material was eluted with 2× sample buffer (Invitrogen) containing 2% β-mercaptoethanol (10 minutes at 70° C.). Immunoisolates from cell extracts were electrophoresed on 10% MES gels (Invitrogen) while for conditioned media immunoprecipitates 7% Tris-Acetate gels (Invitrogen) were used. After SDS-PAGE, gels were dried and radiolabeled bands were detected using a PhosphorImager™ (Molecular Dynamics, Inc.) and analyzed using ImageQuaNT™ 5.1. Levels of APP fragments (secreted Aβ, sAPPβ and APP-CTF) were normalized to the expression level of full-length APP. Data are presented as mean±SEM.

Retroviral Infection

Constructs containing the human ARF6 WT and T157A proteins preceded by the HA-tag were kindly provided by J. Donaldson (Laboratory of Cell Biology, NHLBI, National Institutes of Health, Bethesda, Md. 20892, USA). Human ARF6 constructs were cloned in the retroviral vector pMSCV*-puromycin (Clontech Laboratories; containing an extended multiple cloning site). Cloned pMSCV*-constructs, verified by sequencing, were used for the generation of retroviral particles via co-transfection with the helper plasmid pIκ (Ecopac) in HEK293T cells for packaging of the retroviruses. Viruses were harvested, and particles were either used directly or snap-frozen and aliquots were stored at −80° C. until use. PSEN1 and 2 dKO MEFs were used for transduction with retrovirus for 24 hours followed by puromycin selection in Dulbecco's modified Eagle's medium-F12 supplemented by 10% FCS and 5 µg/ml puromycin, and later sub-cloned to obtain single colonies with the same genetic background.

Cloning of Human ARF6 WT-HA in pMSCV*
Cloning of human ARF6 WT-HA in pGEMt
Strategy:
  Digestion of pCDNA3.1+ARF6 WT-HA with ECORI and XbaI
  Klenow of ARF6 WT-HA fragment
  Adding an A-overhang using TAQ to ARF6 WT-HA fragment
  Ligation of insert in pGEMt vector
Cloning of human ARF6 WT-HA in pMSCV*
Strategy:
  Digestion of vector pMSCV* and pGEMt+ARF6 WT-HA with NcoI and SalI
  Ligation of ARF6 WT-HA into pMSCV*
Oligo's

```
pGEM-T Forward = 2261 =
                                        (SEQ ID NO: 3)
TAA TAC GAC TCA CTA TAG GGC GA pGEM-T Reverse = 2262 =
                                        (SEQ ID NO: 4)
AAG CTA TTT AGG TGA CAC TAT AGA A pMSCV Forward = 2259 =
                                        (SEQ ID NO: 5)
CCCTTGAACCTCCTCGTTCGACC pMSCV Reverse = 2260 =
                                        (SEQ ID NO: 6)
GAGACGTGCTACTTCCATTTGTC
```

Cloning of Human ARF6 T157A-HA in pMSCV*
Normal site directed mutagenese on template pGEM-t+ARF6 WT-HA
Colony PCR with Forward and Reverse pGemt primers
Digestion of vector pMSCV* and pGEMt+ARF6 T157A-HA with NcoI and SalI
Ligation
Oligo's:

```
wa 2322_ARF6wt_T157A_F:
                                        (SEQ ID NO: 7)
CCTCCTGTGCCGCCTCAGGGGACG wa 2323_ARF6wt_T157A_R:
                                        (SEQ ID NO: 8)
CGTCCCCTGAGGCGGCACAGGAGGG pGEM-T Forward = 2261 =
                                        (SEQ ID NO: 9)
TAA TAC GAC TCA CTA TAG GGC GA pGEM-T Reverse = 2262 =
                                        (SEQ ID NO: 10)
AAG CTA TTT AGG TGA CAC TAT AGA A
```

Lentiviral Infection

SMARTvector Lentiviral shRNA particles (thermo-scientific) were used for the stable knockdown of ARF6 in WT MEFs via lentiviral transduction. Different MOIs were used to obtain the best possible knockdown, following the manufacturing protocol. Stable cell lines were obtained after puromycin selection in Dulbecco's modified Eagle's medium-F12 supplemented by 10% FCS and 5 μg/ml puromycin, and later sub-cloned to obtain single colonies with the same genetic background.

Biological Valorization Assays

MEFs will be plated out in 96-well plates and treated with DSMO or DSMO+active compound (concentration range as above) for 24 or 48 hours and next processed for the listed read-outs.

To localize caveolin 1 (Del Pozo et al., 2005), after treatment, cells will be fixed (4% paraformaldehyde/4% sucrose in PBS, 20 minutes RT), permeabilized (0.1% Triton in PBS, 5 minutes RT) and blocked (2% bovine serum albumin (BSA), 2% fetal bovine serum (FBS), 1% gelatin, 2% goat serum in PBS, 1 hour, RT). Primary antibody to caveolin 1 and tubulin (as a control) will be diluted in the same blocking buffer and applied to fixed cells (4° C. overnight). Following washes in PBS, immunolabel will be visualized using appropriate secondary antibodies conjugated to either Alexa-488, -568, -647 or Pacific Blue (Invitrogen) diluted in blocking buffer (1 hour, RT). Finally, cells will be analyzed on the InCell 2000, or alternatively on the Zeiss Radiance2100 confocal microscope. Data acquisition and processing will be with Lasersharp, ImageJ and Photoshop.

To identify acidic compartments, live cells will be, after treatment with the lead compounds (same concentration range and incubation time), incubated with Lysotracker Red (Invitrogen) for 1 hour at 37° C. in normal growth medium containing 0.2 μM LysoTracker (Molecular Probes; Invitrogen). Cells are washed with PBS-/- and fixed with 4% paraformaldehyde for 20 minutes at room temperature and processed for imaging.

To monitor fluorescently tagged EGF (Invitrogen), pulse-chase experiments are performed. Cells are labeled at 4° C. with xng/ml labeled EGF for 10 minutes, and briefly washed with PBS-/- before the chase period starts. EGF-488 is chased for 10, 30 and 60 minutes at 37° C., later fixed with 4% paraformaldehyde for 20 minutes at room temperature and processed for imaging accordingly.

To quantify APP processing products (secreted Aβ, soluble APP ectodomain fragments and APP-Carboxyterminal fragments (CTF) (Annaert et al., 1999), cells are transfected 24 hours after compound treatment with pcDNA-APPsw. Twenty-four hours later, cells are washed twice with serum-free and once with methionine- and cysteine-free medium (Sigma) supplemented with 2 mM L-glutamine, 0.5 mM sodium pyruvate, and Pen/Strep (100 units/ml) (Invitrogen) and incubated (10 minutes at 37° C.). Medium are replaced with the same fresh methionine- and cysteine-free medium (Sigma) but additionally supplemented with 0.07 mCi [$S^{35}$] translabel (EasyTag Express Protein labeling Mix, Perkin Elmer). After 3 hours at 37° C., the conditioned medium is collected and the cell layer washed once in PBS, and then scraped in extraction buffer (1× Tris-buffered saline (TBS: 50 mM Tris.HCl (pH 7.4) and 150 mM NaCl), 1% Triton X-100, Complete protease inhibitor cocktail (Roche Diagnostics)). Both the conditioned media and cell extracts are centrifuged (14,000 rpm, 20 minutes) to remove detached cells and unsolubilized material. Cleared conditioned media are first immunoprecipitated with mab 4G8, then the unbound fraction is split in two and used to immunoisolate secreted APPβ ectodomain and Aβ peptides using pab AND (4 μl) (Rajendran et al., 2006) and 6E10 (3 μl), respectively, together with protein G-Sepharose (Pharmacia) (overnight, at 4° C., on a rotating wheel). Full-length APP and APP-CTFs are isolated likewise from extracts using pab B63. Immunoprecipitates are washed five times in extraction buffer, once in TBS, and bound material was eluted with 2× sample buffer (Invitrogen) containing 2% β-mercaptoethanol (10 minutes at 70° C.). Immunoisolates from cell extracts are electrophoresed on 10% MES gels (Invitrogen) while for conditioned media immunoprecipitates 7% Tris-Acetate gels (Invitrogen) are used. After SDS-PAGE, gels are dried and radiolabeled bands detected using a PhosphorImager (Molecular Dynamics, Inc.) and analyzed using ImageQuaNT™ 5.1. Levels of APP fragments (secreted Aβ, sAPPβ and APP-CTF) are normalized to the expression level of full-length APP.

Assay Development

A screening assay is set up that can be dissected in different steps. First, cells are brought into culture and several cell lines are maintained. These cells are treated with compounds, incubated and afterwards fixed and stained. These stained cells are imaged and the images are further analyzed.

Maintaining of MEF cell cultures. MEF (mouse embryonic fibroblasts) cell lines are passaged (every 3 days at confluency of 90%) under sterile circumstances in T75 bottles appropriate for adhering cells. Two T75 bottles were used per cell line to provide enough cells for the experiments. A sterile environment is created by usage of a LAF-cabinet (laminar airflow cabinet) and a solution of 70% ethanol. First, the cells are washed with phosphate-buffered saline (PBS[−]$CaCl_2$[−]$MgCl_2$) to remove dead cells and remaining medium. After trypsinizing the cells two or three minutes, fresh DMEM+L-glutamine+HEPES+10% FBS+PENSTREP medium is added to inactivate the trypsin activity. Then, a part of the cell suspension is transferred to a new bottle with fresh medium. In MEF PSdKO+hArf6 c1.10 cells, 5 µg/µL puromycin is added to keep them selected for ARF6 expression. All cell suspensions are maintained at 37° C. and passed through a cell strainer to obtain single cells. The concentration of this cell suspension is calculated by usage of a Neubauer improved hemacytometer. This cell suspension is diluted to 200,000 cells/ml. At least 3 ml cell suspension of each cell line at this concentration is needed to manually plate 19 µl/well into a 384-well-plate.

Liquid handling. To handle the 384-well plates, the Freedom EVOware 150 pipetting robot (TECAN) is used according to the manufacturer's instructions. In these experiments, only the multichannel head and the washing station are used to dilute the compounds of the master plate, to treat the cells with compounds, to fix the cells and to stain them afterwards.

Treat cells with compounds. First, the master plate with compounds (96-well plate) is diluted so the concentration of the compounds is lowered from 25 mM to 1000 µM. Two 384-well plates are used to perform the experiment in duplicate, the cells are manually added with a multichannel pipette (8 channels). After 12 hours in culture, the cells are attached to the bottom of the 384-well plate and ready to be treated. Every cell line in one plate is treated once with a final concentration of 50 µM of every compound. Again, the cells are incubated for 24 hours in a $CO_2$ incubator. All three different cell lines and a negative control, consisting of DMSO, are plated in a 384-well plate. The wells only filled with DMSO serve as negative controls for the fluorescence of the compounds. The first (1 and 2) and last (23 and 24) two columns contain cells but are not treated with compound so they serve as negative controls for the cell morphology. This plate is made twice to provide duplicate experiments.

Fixing and staining. After the incubation of the cells with compounds, they are fixed for 15 minutes with a 4% PFH (paraformaldehyde) solution. To stain the cells, the liquid is first removed from the fixed cells, followed by three washes with PBS[+]$CaCl_2$[+]$MgCl_2$. A 0.1% Triton X-100 solution (in PBS[+]$CaCl_2$[+]$MgCl_2$) is added to permeabilize the cells and to allow phalloidin-TRITC to enter the cells. After an incubation time of three minutes, the cells are washed twice with PBS[+]$CaCl_2$[+]$MgCl_2$. Before adding the dye, aspecific interactions are avoided by incubating the cells for 15 minutes with blocking buffer (PBS[−]$CaCl_2$[−]$MgCl_2$ containing+2% BSA+2% FBS+0.2% gelatin). Now, the phalloidin-TRITC dye diluted to 1 µL/500 µL from a 2.5 mg/mL stock solution (with PBS[+]$CaCl_2$[+]$MgCl_2$), is added to the cells and incubated for 25 minutes. The final concentration of the dye is 0.005 mg/mL. After staining the cells with phalloidin, a DAPI staining was performed as a control. First, the phalloidin dye was removed and the cells were washed again twice with PBS[+]$CaCl_2$[+]$MgCl_2$. A DAPI stock solution of 1 mg/mL is diluted at a rate of 1 µL/700 µL (in PBS[+]$CaCl_2$[+]$MgCl_2$). This staining solution is added to the cells. Because the used dyes are fluorescent, they lose some of their strength when exposed to light; so they are covered with aluminum foil and stored in the refrigerator. Every time a liquid is used, a volume of 50 µL is added.

Imaging. After fixing and staining, images were taken with the InCell Analyzer 2000 (GE Healthcare). These images were obtained from 384-well plates with a 10× objective lens (Nikon 10×—NA 0.45—Plan Apo—CFI/60), a large chip CCD camera (CoolSNAP K4™—2048×2048 pixel array—7.40 µm square pixel) and the QUAD 1 polychroic mirror. To save time, two fields per well were imaged and for focusing, the hardware autofocus (laser) was used. For the phalloidin-TRITC staining, three wavelengths were used. The DAPI excitation and emission filters were used with an exposure time of 0.050 second. The Cy3 excitation and emission filters were used with an exposure time of 2,000 seconds and the brightfield excitation (transmitted light) and the DAPI emission filter were used with an exposure time of 0.050 second to obtain a brightfield image.

Analysis. The acquired images were further automatically analyzed with the InCell Workstation 3.5 software (GE Healthcare, Amersham, United Kingdom). For the analysis, five parameters are calculated to study changes in the cell morphology, namely the cell intensity, cell count, cell roundness, cell area (size) and cell elongation (length). The ratio of the short over the long axis of the cells is called the cell elongation. A non-elongated or symmetric cell has a value of one. All of the other values situate between zero and one. The cell roundness is also called the cell 1/form factor. It is calculated via parameter (perimeter) over area. These values lie between one and +infinity. A cell with a roundness of one, forms a perfect circle.

Compounds. The compound screening collection at the Compound Screening Facility of VIB (Gent, BE) amounts to a total of 42,000 compounds. The collection comprises three different chemical libraries acquired through ChemBridge Corporation (WorldWideWeb.chembridge.com/chembridge/); DIVERSet™ (22,000 compounds), CNS-Set™ (10,000 compounds) and NOVACore (10,000 compounds). For selection of the DIVERSet™ compounds, a range of filtering methods are applied to ensure maximal diversity with a minimal number of compound, and to remove unstable, toxic and non-drug-like compounds. The DIVERSet™ library can be used in initial screening programs that require high diversity and qualitative lead-like compounds. For the CNS-Set™ library, additional computational methods are applied to select compounds with increased probability of oral bioavailability and blood-brain-barrier penetration. NOVACore™ is a diverse and drug-like library comprising compounds that are synthesized via combinatorial chemistry. The main focus of NOVACore™ is "novelty"; all compounds are recently synthesized by ChemBridge and contain mainly proprietary ChemBridge building blocks. All NOVACore™ compounds have a low molecular weight, which allows more margin for further lead optimization.

REFERENCES

Annaert W. G., et al. Presenilin 1 controls γ-secretase processing of the amyloid precursor protein in pre-Golgi compartments of hippocampal neurons. *J. Cell Biol.* 147(2): 277-294, 1999.

Balasubramanian, N., et al., ARF6 and microtubules in adhesion-dependent trafficking of lipid rafts. *Nat. Cell Biol.* 9:1381-91 (2007).

Bartus R. T., R. L. Dean, 3rd, B. Beer, A. S. Lippa. The cholinergic hypothesis of geriatric memory dysfunction. *Science* 217:408 (1982).

Bonifacino J. S. (2004). "The GGA proteins: adaptors on the move." *Nat. Rev. Mol. Cell Biol.* 23-32.

Brown F. D., A. L. Rozelle, et al. (2001). "Phosphatidylinositol 4,5-bisphosphate and ARF6-regulated membrane traffic." *J. Cell Biol.* 154(5):1007-17.

Capell A., H. Steiner, et al. (2000). "Maturation and propeptide cleavage of beta-secretase." *J. Biol. Chem.* 275 (40):30849-54.

Carey R. M., B. A. Balcz, et al. (2005). "Inhibition of dynamin-dependent endocytosis increases shedding of the amyloid precursor protein ectodomain and reduces generation of amyloid beta protein." *BMC Cell Biol.* 6:30.

D'Souza-Schorey C. and P. Chavrier (2006). "ARF proteins: roles in membrane traffic and beyond." *Nat. Rev. Mol. Cell Biol.* 7(5):347-58.

Del Pozo M. A. et al., Integrins regulate Rac targeting by internalization of membrane domains. *Science*, 303, p. 839-42 (2004).

del Pozo M. A., et al., Phospho-caveolin-1 mediates integrin-regulated membrane domain internalization. *Nat. Cell Biol.* 2005. 7(9):901-8.

De Strooper, Aph-1, Pen-2, and Nicastrin with Presenilin generate an active gamma-Secretase complex. *Neuron* 38:9-12 (2003).

Esselens et al. *J. Cell Biology*, 2004 September; 166(7):1041-1054.

Franco M., P. J. Peters, et al. (1999). "EFA6, a sec7 domain-containing exchange factor for ARF6, coordinates membrane recycling and actin cytoskeleton organization." *Embo. J.* 18(6):1480-91.

Frittoli E., A. Palamidessi, et al. (2008). "The primate-specific protein TBC1D3 is required for optimal macropinocytosis in a novel ARF6-dependent pathway." *Mol. Biol. Cell* 19(4):1304-16.

Golde T. E., D. Dickson, M. Hutton. Filling the gaps in the abeta cascade hypothesis of Alzheimer's disease. *Curr. Alzheimer Res.* 3:421-30 (2006).

Grande-Garcia A. et al., Caveolin-1 regulates cell polarization and directional migration through Src kinase and Rho GTPases. *J. Cell Biol.*, 177:683-94 (2007).

Grant B. D. and J.-G. Donaldson (2009). "Pathways and mechanisms of endocytic recycling." *Nat. Rev. Mol. Cell Biol.* 10(9):597-608.

Hardy J., D. J. Selkoe, The amyloid hypothesis of Alzheimer's disease: progress and problems on the road to therapeutics. *Science* 297:353-6 (2002).

Hashimoto S., et al., Requirement for ARF6 in breast cancer invasive activities. *Proc. Acad. Sci. U.S.A.* 2004. 101(17): 6647-52.

He X., W. P. Chang, et al. (2002). "Memapsin 2 (beta-secretase) cytosolic domain binds to the VHS domains of GGA1 and GGA2: implications on the endocytosis mechanism of memapsin 2." *FEBS Lett* 524(1-3)183-7.

He X., F. Li, et al. (2005). "GGA proteins mediate the recycling pathway of memapsin 2 (BACE)." *J. Biol. Chem.* 280(12): 11696-703.

Huse J. T., D. S. Pijak, et al. (2000). "Maturation and endosomal targeting of beta-site amyloid precursor protein-cleaving enzyme. The Alzheimer's disease beta-secretase." *J. Biol. Chem.* 275(43):33729-37.

Iwatsubo T., A. Odaka, N, Suzuki, H. Mizusawa, N. Nukina, Y. Ihara, Visualization of A beta 42(43) and A beta 40 in senile plaques with end-specific A beta monoclonals: evidence that an initially deposited species is A beta 42(43). *Neuron* 13:45-53 (1994).

Jackson T. R., F. D. Brown, et al. (2000). "ACAPs are arf6 GTPase-activating proteins that function in the cell periphery." *J. Cell Biol.* 151(3):627-38.

Jaworski J. (2007). ARF6 in the nervous system. *J. Cell Biol.* 86:513-524.

Kabat E. A., T. T. Wu, Identical V region amino acid sequences and segments of sequences in antibodies of different specificities. Relative contributions of VH and VL genes, minigenes, and complementarity-determining regions to binding of antibody-combining sites. *The Journal of Immunology* 147(5):1709-19 (1991).

Lanzetti L., et al., Rab5 is a signaling GTPase involved in actin remodelling by receptor tyrosine kinases. *Nature* 2004. 429(6989):309-14.

Mullan M., F. Crawford, et al. (1992). "A pathogenic mutation for probable Alzheimer's disease in the APP gene at the N-terminus of beta-amyloid." *Nat. Genet.* 1(5):345-347.

Naslavsky N., R. Weigert, et al. (2003). "Convergence of non-clathrin- and clathrin-derived endosomes involves ARF6 inactivation and changes in phosphoinositides." *Mol. Biol. Cell* 14(2):417-31.

Naslavsky N., R. Weigert, et al. (2004). "Characterization of a non-clathrin endocytic pathway: membrane cargo and lipid requirements." *Mol. Biol. Cell* 15(8):3542-52.

Ohno M., E. A. Sametsky, L. H. Younkin, H. Oakley, S. G. Younkin, M. Citron, R. Vassar, J. F. Disterhoft. BACE1 Deficiency Rescues Memory Deficits and Cholinergic Dysfunction in a Mouse Model of Alzheimer's Disease. *Neuron* 41:27-33 (2004).

Ohno M., L. Chang, W. Tseng, H. Oakley, M. Citron, W. L. Klein, R. Vassar, J. F. Disterhoft. Temporal memory deficits in Alzheimer's mouse models: rescue by genetic deletion of BACE1. *Eur. J. Neurosci.* 23:251-260 (2006).

Pastorino L., A. F. Ikin, et al. (2002). "The carboxyl-terminus of BACE contains a sorting signal that regulates BACE trafficking but not the formation of total A(beta)." *Mol. Cell Neurosci.* 19(2):175-85.

Peters P. J., V. W. Hsu, et al. (1995). "Overexpression of wild-type and mutant ARF1 and ARF6: distinct perturbations of nonoverlapping membrane compartments." *J. Cell Biol.* 128(6):1003-17.

Rajendran L., M. Honsho, et al. (2006). "Alzheimer's disease beta-amyloid peptides are released in association with exosomes." *Proc. Natl. Acad. Sci. U.S.A.* 103(30)11172-7.

Rink J., E. Ghigo, et al. (2005). "Rab conversion as a mechanism of progression from early to late endosomes." *Cell* 122(5):735-749.

Roberds S. L., J. Anderson, G. Basi, M. J. Bienkowski, D. G. Branstetter, K. S. Chen, S. B. Freedman, N. L. Frigon, D. Games, K. Hu, et al. BACE knockout mice are healthy despite lacking the primary β-secretase activity in brain: implications for Alzheimer's disease therapeutics. *Hum. Mol. Genet.* 10:1317-1324 (2001).

Schneider A., L. Rajendran, et al. (2008). "Flotillin-dependent clustering of the amyloid precursor protein regulates its endocytosis and amyloidogenic processing in neurons." *J. Neurosci.* 28(11):2874-82.

Selkoe D. J., Alzheimer's disease: genes, proteins, and therapy. *Physiol. Rev.* 81:741-66 (2001).

Shiba T., S. Kametaka, et al. (2004). "Insights into the phosphoregulation of beta-secretase sorting signal by the VHS domain of GGA1." *Traffic* 5(6):437-48.

Stenmark H., R. G. Parton, et al. (1994). "Inhibition of rab5 GTPase activity stimulates membrane fusion in endocytosis." *Embo. J.* 13(6)1287-1296.

Tesco G., Y. H. Koh, et al. (2007). "Depletion of GGA3 stabilizes BACE and enhances beta-secretase activity." *Neuron* 54(5):721-37.

Traub L. M. (2009). "Tickets to ride: selecting cargo for clathrin-regulated internalization." *Nat. Rev. Mol. Cell Biol.* 10(9):583-96.

von Arnim C. A., M. M. Tangredi, et al. (2004). "Demonstration of BACE (beta-secretase) phosphorylation and its interaction with GGA1 in cells by fluorescence-lifetime imaging microscopy." *J. Cell Sci.* 117 (Pt. 22):5437-45.

Wahle T., K. Prager, et al. (2005). "GGA proteins regulate retrograde transport of BACE1 from endosomes to the trans-Golgi network." *Mol. Cell Neurosci.* 29(3):453-61.

Wilson et al. *J. Cell Biology*, 2004 May; 165(3):335-346.

Winter G., W. J. Harris, Humanized antibodies. *Trends Pharmacol Sci.* 14(5):139-43 (1993).

Zhao X., T. Greener, et al. (2001). "Expression of auxilin or AP180 inhibits endocytosis by mislocalizing clathrin: evidence for formation of nascent pits containing AP1 or AP2 but not clathrin." *J. Cell Sci.* 114(Pt 2): 353-65.

---

The invention claimed is:

1. A method of identifying compounds that modulate endosomal redistribution, the method comprising:
   administering a test compound to a first cell culture and a second cell culture;
   wherein the first and second cell cultures lack endogenous presenilin expression or function; and
   wherein only one of the first and second cell cultures stably expresses ADP-ribosylation factor 6 (ARF6);
   imaging at least one morphological parameter of the cells in the first cell culture; and
   imaging the at least one morphological parameter of the cells in the second cell culture;
   wherein, a deviation in the at least one morphological parameter between the first and second cell cultures identifies the test compound as a compound that modulates endosomal redistribution.

2. The method according to claim 1, further comprising:
   determining the effect of the test compound on ARF6 cycling activity and/or ARF6 effector protein activity, and
   measuring the amount of amyloid beta peptide produced by the cell culture.

3. The method according to claim 2, wherein the ARF6 effector protein is selected from the group consisting of a GAP, GIT-1, a GEF, and EFA6A.

4. The method according to claim 1, further comprising:
   a compound identified is a therapeutic candidate for treating Alzheimer's disease.

5. The method according to claim 1, further comprising:
   imaging the at least one morphological parameter in a corresponding wild type cell cuture;
   wherein a deviation in the at least one morphological parameter between the cell culture lacking stable expression of ARF6 and the wild-type cell identifies the test compound as a compound that modulates endosomal redistribution.

6. A method of identifying a compound that reduces amyloid beta peptide formation in a mammalian cell, the method comprising:
    administering a test compound to a cell culture lacking endogenous presenilin expression and/or function;
    determining the effect of the test compound on ADP-ribosylation factor 6 (ARF6) cycling activity and/or ARF6 effector protein activity, and
    measuring the amount of amyloid beta peptide produced by the cell culture.

7. The method according to claim 6, wherein the ARF6 effector protein is selected from the group consisting of a GAP, GIT-1, a GEF, and EFA6A.

8. The method according to claim 6, wherein the mammalian cell is in a subject suffering from Alzheimer's disease.

9. The method according to claim 6, wherein the compound is a therapeutic candidate for treating Alzheimer's disease.

10. A method of identifying compounds that modulate endosomal redistribution, the method comprising:
    administering a test compound to a first cell culture and a second cell culture;
    wherein only one of the first and second cell cultures lacks endogenous presenilin expression or function;
    imaging at least one morphological parameter of the cells in the first cell culture; and
    imaging the at least one morphological parameter of the cells in the second cell culture;
    wherein, a deviation in the at least one morphological parameter between the first and second cell cultures identifies the test compound as a compound that modulates endosomal redistribution.

* * * * *

SEQUENCE LISTING

```
<160> NUMBER OF SEQ ID NOS: 10

<210> SEQ ID NO 1
<211> LENGTH: 21
<212> TYPE: DNA
<213> ORGANISM: Homo sapiens

<400> SEQUENCE: 1
gcaccgcatt atcaatgacc g                                            21

<210> SEQ ID NO 2
<211> LENGTH: 19
<212> TYPE: DNA
<213> ORGANISM: Homo sapiens

<400> SEQUENCE: 2
ggtctcatct tcgtagtgg                                               19

<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3
taatacgact cactataggg cga                                          23

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
aagctattta ggtgacacta tagaa                                        25

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
cccttgaacc tcctcgttcg acc                                          23

<210> SEQ ID NO 6
<211> LENGTH: 23
```

```
<212> TYPE: DNA
<213> ORGANISM: Artificial Sequence
<220> FEATURE:
<223> OTHER INFORMATION: Primer

<400> SEQUENCE: 6
gagacgtgct acttccattt gtc                                        23

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
cctcctgtgc cgcctcaggg gacg                                       24

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
cgtcccctga ggcggcacag gaggg                                      25

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
taatacgact cactataggg cga                                        23

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10
aagctattta ggtgacacta tagaa                                      25
```